(12) United States Patent
Andrieux et al.

(10) Patent No.: US 8,393,323 B2
(45) Date of Patent: Mar. 12, 2013

(54) SUPPLEMENTAL GAS SAFETY SYSTEM FOR A BREATHING ASSISTANCE SYSTEM

(75) Inventors: Claude Andrieux, Bordes (FR); Cedric Jourdain, Lons (FR)

(73) Assignee: Covidien LP, Mansfield, MA (US)

( * ) Notice: Subject to any disclaimer, the term of this patent is extended or adjusted under 35 U.S.C. 154(b) by 1045 days.

(21) Appl. No.: 12/242,781

(22) Filed: Sep. 30, 2008

(65) Prior Publication Data

US 2010/0078026 A1    Apr. 1, 2010

(51) Int. Cl.
*A61M 11/00* (2006.01)

(52) U.S. Cl. .............................. 128/204.21; 128/204.18

(58) Field of Classification Search ............. 128/204.18, 128/204.21, 204.23, 204.26, 203.12
See application file for complete search history.

(56) References Cited

U.S. PATENT DOCUMENTS

| | | | |
|---|---|---|---|
| 4,201,204 A | 5/1980 | Rinne et al. | 128/203.27 |
| 6,269,811 B1* | 8/2001 | Duff et al. | 128/204.21 |
| 7,487,774 B2* | 2/2009 | Acker | 128/204.18 |
| 2007/0107728 A1* | 5/2007 | Ricciardelli et al. | 128/204.21 |

FOREIGN PATENT DOCUMENTS

| | | |
|---|---|---|
| EP | 1 014 527 A2 | 6/2000 |
| EP | 1 338 297 A1 | 8/2003 |
| GB | 1 034 983 | 7/1966 |
| WO | 2006/012878 A1 | 2/2006 |
| WO | 2009/085995 | 7/2009 |

OTHER PUBLICATIONS

International PCT Search Report and Written Opinion, PCT/US2009/055287, 17 pages, Mailed Feb. 12, 2009.

* cited by examiner

*Primary Examiner* — Steven Douglas

(57) ABSTRACT

A system for managing a supplemental gas supply in a breathing assistance system configured to provide breathing assistance to a patient includes a temperature sensor and a control system. The temperature sensor is configured to measure a temperature associated with a breathing assistance system configured to deliver a first gas and a supplemental gas toward a patient. The control system is configured to automatically control the flow of the supplemental gas based at least on the monitored temperature.

21 Claims, 13 Drawing Sheets

US 8,393,323 B2

SUPPLEMENTAL GAS SAFETY SYSTEM FOR A BREATHING ASSISTANCE SYSTEM

TECHNICAL FIELD

The present disclosure is related to breathing assistance systems, and more particularly to a supplemental gas safety system for a breathing assistance system.

BACKGROUND

Breathing assistance systems are used to provide various types of breathing assistance to patients. For example, a ventilator provides mechanical ventilation to a patient by delivering pressurized gas (e.g., air and/or supplemental oxygen) to the patient through a breathing circuit connected to the patient by a connection device, e.g., an endotracheal tube or a nose or face mask. A ventilator may provide ventilation according to any of a variety of well-known ventilation modes, e.g., assist/control (A/C) ventilation, volume controlled ventilation, pressure controlled ventilation, and synchronous intermittent mandatory ventilation (SIMV) ventilation. Each of such modes may provide or allow for one or more types of breaths, including mandatory breaths, assisted breaths, and/or spontaneous breaths.

Another example breathing assistance system is a continuous positive airway pressure (CPAP) system. CPAP therapy has become a common prescription for individuals suffering from sleep apnea and/or other breathing ailments. Such therapy may involve placement of a nose or face mask on the subject during sleeping, while positive pressure air is continuously delivered from a CPAP box to the patient through a breathing circuit connected to the patient by a connection device, e.g., a nose or face mask. In this manner, positive pressure air may be delivered to the patient's upper airway in order to prevent the upper airway tissues from collapsing during sleep, thus reducing the occurrence and/or severity of sleep apnea.

SUMMARY

According to one embodiment of the present disclosure, a method for managing a supplemental gas supply in a breathing assistance system configured to provide breathing assistance to a patient is provided. The method includes monitoring a temperature associated with a breathing assistance system configured to deliver a first gas and a supplemental gas toward a patient, and automatically controlling the flow of the supplemental gas based at least on the monitored temperature.

According to another embodiment of the present disclosure, a system for managing a supplemental gas supply in a breathing assistance system configured to provide breathing assistance to a patient includes a temperature sensor and a control system. The temperature sensor is configured to measure a temperature associated with a breathing assistance system configured to deliver a first gas and a supplemental gas toward a patient. The control system is configured to automatically control the flow of the supplemental gas based at least on the monitored temperature.

According to another embodiment of the present disclosure, a breathing assistance system for providing breathing assistance to a patient is provided. The breathing assistance system may include a system for delivering a flow of a first gas and a supplemental gas toward a patient, and a supplemental gas safety system for managing a supplemental gas supply in the breathing assistance system. The supplemental gas safety system may include a temperature sensor configured to measure a temperature associated with the breathing assistance system, and a control system configured to automatically control the flow of the supplemental gas based at least on the monitored temperature.

BRIEF DESCRIPTION OF THE DRAWINGS

Some embodiments of the disclosure may be understood by referring, in part, to the following description and the accompanying drawings, in which like reference numbers refer to the same or like parts and wherein.

DETAILED DESCRIPTION

Selected embodiments of the disclosure may be understood by reference, in part, to FIGS. 1-13B, wherein like numbers refer to same and like parts.

Figure 1:
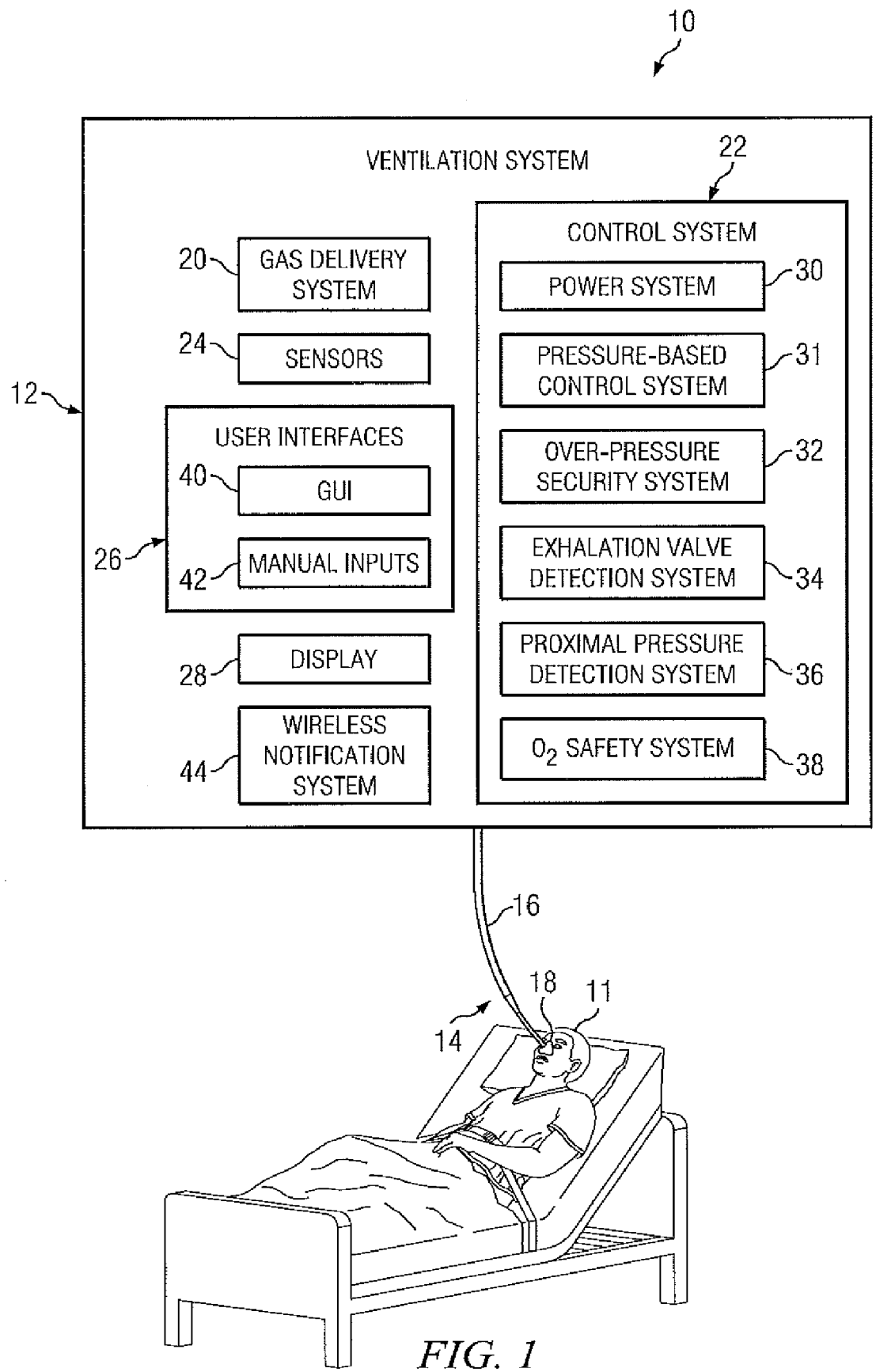
FIG. 1 illustrates an example breathing assistance system for providing breathing assistance to a patient, according to one embodiment of the disclosure.

FIG. 1 illustrates an example breathing assistance system 10 for providing breathing assistance to a patient, according to one embodiment of the disclosure. Breathing assistance system 10 may be generally configured to provide one or more types of ventilation to the patient. As used herein, "ventilation" means communicating gas to and/or from a patient 11 to provide any type of breathing assistance to the patient 11, including, e.g., mechanically ventilating the patient and/or treating an apnea or other breathing condition of the patient. "Ventilation" includes breathing assistance typically provided by a ventilator, as well as breathing assistance typically provided by CPAP device. Thus, as discussed below, breathing assistance system 10 may provide any or all of the following:

Positive Pressure ventilation;
Assist/Control, SIMV, and/or CPAP modes of ventilation;
Breath types including Volume, Pressure Control, and Pressure Support;
Other types or modes of ventilation and/or other breath types.

In example embodiments, breathing assistance system 10 may provide some or all of the following user-selectable ventilation modes:

Assisted Controlled Volume (VOLUME A/C);
Assisted Controlled Pressure (PRESSURE A/C);
Synchronous Intermittent Mandatory Ventilation Volume (V SIMV);
Synchronous Intermittent Mandatory Ventilation Pressure (P SIMV);
Continuous Positive Airway Pressure (CPAP); and
Pressure Support Ventilation (PSV).

Breathing assistance system 10 may be configured for use by both adult and pediatric patients 11. In addition, in certain embodiments, breathing assistance system 10 may be configured for use in institutional, home, and/or portable settings.

As shown in FIG. 1, breathing assistance system 10 may include a ventilation system 12 and a connection system 14 for connecting ventilation system 12 to patient 11.

Ventilation system 12 may comprise any device, apparatus, or system for providing ventilation to a patient 11 via connection system 14. Connection system 14 may be generally configured to deliver gas from ventilation system 12 to patient 11 and/or to communicate exhaust gas away from patient 11. For example, connection system 14 may comprise any suitable type of breathing circuit 16 (e.g., a single-limb or dual-limb breathing circuit) and/or a patient connection apparatus 18. For instance, connection system 14 may include a 6-foot (single-limb or dual-limb) breathing circuit 16. In embodiments using a dual-limb breathing circuit 16, both limbs (the inspiratory limb and the expiratory limb) may be connected to ventilation system 12, as discussed below with reference to FIG. 2.

A patient connection apparatus 18 may include any device or devices configured to connect breathing circuit 16 to one or more breathing passageways of patient 11. For example, patient connection apparatus 18 may include a patient connection tube directly connected to the patient's trachea, an artificial airway (e.g., an endotracheal tube or other device) inserted in the patient's trachea, and/or a mask, cushion or nasal pillows positioned over the patient's nose and/or mouth.

Ventilation system 12 may include a gas delivery system 20, a control system 22, sensors 24, user interfaces 26, a display system 28, and a wireless notification module 44.

Gas delivery system 20 may include any device or devices configured to generate, supply, and/or deliver gas (e.g., pressurized air) toward patient 11 via connection system 14. For example, gas delivery system 20 may comprise a device capable of generating pressurized air (e.g., a motorized turbine-based blower or piston-based device), a wall outlet through which pressurized air may be supplied (e.g., in a hospital or clinic), valves configured to control the supply of gas to the patient (e.g., a PSOL or other solenoid valve), one or more tanks of compressed gas, a compressor, or any other suitable source of pressurized or non-pressurized gas. In some embodiments, gas delivery system 20, in cooperation with other components of ventilation system 12 (e.g., an exhalation valve) may generate both positive and negative gas flows toward patient 11. For example, a positive gas flow may be generated as gas is delivered to patient 11 during inhalation, while a negative gas flow may be generated as exhaust gas is communicated from patient 11 during exhalation.

In some embodiments, gas delivery system 20 may be configured to deliver a gas mixture toward patient 11, e.g., a mixture of air and supplemental oxygen or other supplemental gas. Depending on the particular embodiment, the point of mixture for the multiple gasses may be upstream or downstream of gas delivery system 20. For example, a supplemental oxygen stream may be connected to mix with a primary air stream at a point upstream or downstream of gas delivery system 20.

As used herein, the term "gas" may refer to any one or more gases and/or vaporized substances suitable to be delivered to and/or from a patient via one or more breathing orifices (e.g., the nose and/or mouth), such as air, nitrogen, oxygen, any other component of air, $CO_2$, vaporized water, vaporized medicines, and/or any combination of two or more of the above, for example.

As used herein, the term "patient" may refer to any person or animal that may receive breathing assistance from system 10, regardless of the medical status, official patient status, physical location, or any other characteristic of the person. Thus, for example, patients may include persons under official medical care (e.g., hospital patients), persons not under official medical care, persons receiving care at a medical care facility, persons receiving home care, etc.

Control system 22 may include any sub-systems for controlling any aspect of the operation of ventilation system 12, including, e.g., a power system 30, a gas delivery control system 31, an over-pressure security system 32, an exhalation valve detection system 34, a proximal pressure detection system 36, and an oxygen safety system 38.

Each sub-system 30, 31, 32, 34, 36, and 38 of control system 22, may include, or have access to, any suitable controllers, processors, memory devices, and any other suitable hardware, software, and/or firmware for performing any of the function associated with such systems. In particular, each system 30, 31, 32, 34, 36, and 38 may include or have access to any instructions (e.g., software, firmware, algorithms, or other logic or instructions) stored in any suitable tangible storage media and executable by a processor for performing any of the functions associated with that system.

Any one or more sensors 24 may be provided for sensing, detecting, and/or monitoring one or more parameters related to the ventilation of patient 11, e.g., parameters regarding the ventilation provided by ventilation system 12 and/or physiological parameters regarding patient 11. For example, sensors 24 may include one or more devices for measuring various parameters of gas flowing to or from patient 11 or ventilation system 12, e.g., the pressure, flow rate, flow volume, temperature, gas content, and/or humidity of such gas flow.

In certain embodiments, sensors 24 may include one or more pressure sensors and one or more flow sensors for measuring the pressure and flow, respectively, of gas through various components of system 10. Such pressure and flow sensors 24 may be located at any suitable location in system 10. For example, each sensor 24 may be integrated with or coupled to ventilation system 12, integrated with or coupled to connection system 14, coupled to patient 11, or otherwise associated with system 10.

Figure 5:
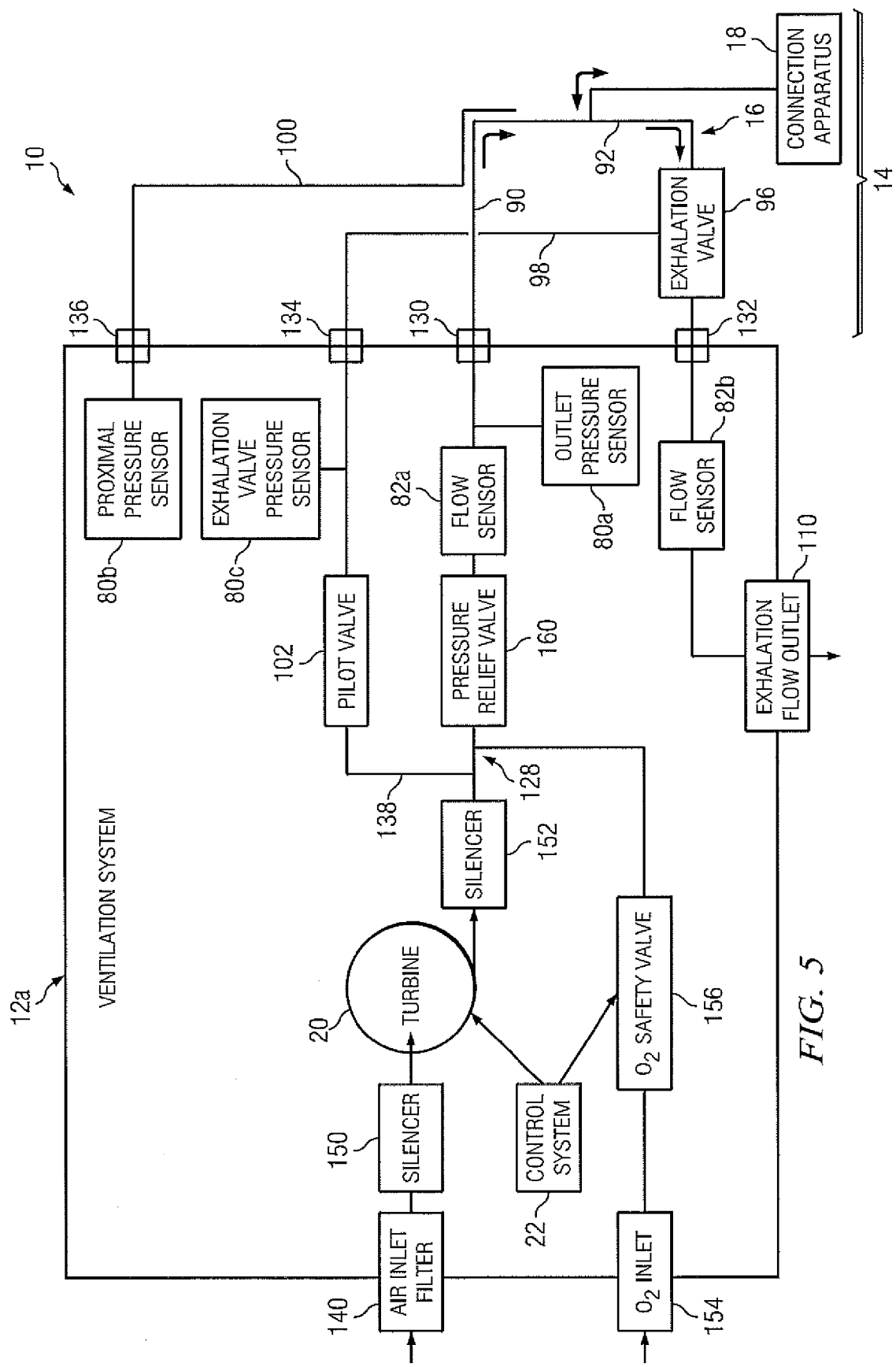
FIG. 5 illustrates a flow path diagram showing various components and gas flow paths in an example embodiment of a ventilation system, according to one embodiment of the present disclosure.
Figure 6:
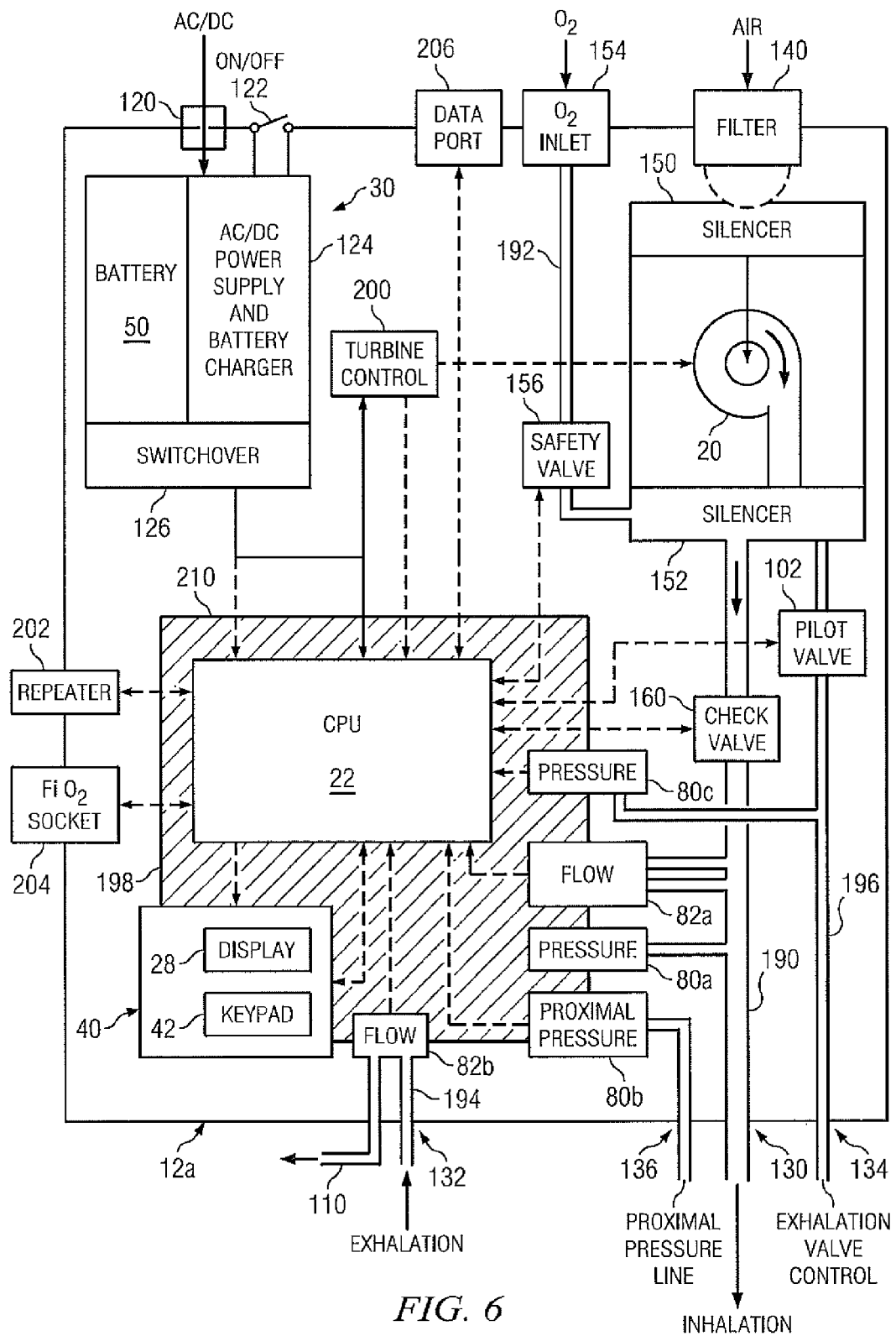
FIG. 6 illustrates an example arrangement of various components of an example ventilation system, according to one embodiment of the present disclosure.

In some embodiments (e.g., as shown in FIGS. 5 and 6), system 10 may include any or all of the following:

(a) a main pressure sensor for measuring the pressure of gas flow exiting ventilation system 12 or gas delivery system 20, or the pressure of gas flow entering connection system 14;

(b) a proximal pressure sensor for measuring pressure at or near the patient end of connection system 14, referred to as the "proximal pressure";

(c) an exhalation valve pressure sensor for measuring pressure in a conduit used for controlling an exhalation valve of system 10;

(d) an inhalation flow sensor for measuring the flow rate of gas flowing toward patient 11 (e.g., via an inhalation limb of breathing circuit 16);

(e) an exhalation flow sensor for measuring the flow rate of gas exhaled by patient 11 (e.g., via an exhalation limb of breathing circuit 16); and/or (f) any other pressure and/or flow sensors.

The main pressure sensor, proximal pressure sensor, and/or exhalation valve pressure sensor may be used to provide various functions of ventilation system 12. For example, as discussed below regarding FIG. 2, signals from the main pressure sensor and the proximal pressure sensor may be used in a first technique for detecting and managing over-pressure of gas in connection system 14 (e.g., in breathing circuit 16). As another example, as discussed below regarding FIG. 2, signals from the exhalation valve pressure sensor may be used in a second technique for detecting and managing over-pressure of gas in connection system 14 (e.g., in breathing circuit 16). As another example, as discussed below regarding FIG. 2, signals from the exhalation valve pressure sensor may be used to detect whether an exhalation valve is present in the current configuration of system 10 (e.g., whether the currently connected breathing circuit 16 includes an exhalation valve). As yet another example, as discussed below regarding FIG. 2, signals from the main pressure sensor and/or the proximal pressure sensor may be used to determine whether proximal pressure may be measured and used by ventilation system 12 (e.g., if a proximal pressure line is properly connected and the proximal pressure sensor is working properly).

User interfaces 26 may include any suitable device or devices allowing a user to interface with breathing assistance system 10, e.g., to control ventilation system 12, to navigate through various display screens, to make selections, and/or to set, modify, or otherwise control various parameters regarding system 10. For example, user interfaces 26 may allow a user to input desired performance parameters (e.g., pressure or flow rate) that may be communicated to control system 22 to control the operation of gas delivery system 20 and/or other components of system 10.

User interfaces 26 may include a graphic user interface (GUI) 40, one or more manual input devices 42 separate from the GUI, and/or any other input devices. In some embodiments, GUI 40 may include a touch screen configured to display various information and provide an interface for accepting input from user (e.g., to navigate through various screens, to make selections, to set or modify various parameters, to change or configure the display, etc.). In embodiments in which GUI 40 does not include a touch screen, manual input devices 42 may be used to make selections and navigate through various screens or menus displayed on GUI 40. Manual input devices 42 may include any physical buttons, knobs, dials, switches, levers, or any other devices that may be manipulated by a user.

Display system 28 may comprise a screen or any other device suitable for visually displaying medical data. For example, display system 28 may include a monitor, an LCD screen, LEDs, or any other visual device. In some embodiments, display system 28 and user interfaces 26 may be at least partially integrated, e.g., where ventilation system 12 includes a touch screen or other GUI 40.

Power system 30 may include or facilitate the connection of one or more sources of power for ventilation system 12, e.g., an external AC power source, an external DC power source, and/or one or more rechargeable batteries, for example. In embodiments including a battery 50, power system 30 may include a battery security system 52 for ensuring that only approved batteries may be used in ventilation system 12 and/or a battery age management system 70 for recording and displaying age data regarding a battery 50, e.g., the number of charge and discharge cycles the battery 50 has experienced. Battery security system 52 and battery age management system 70 are illustrated and discussed in greater detail below with reference to FIG. 3.

Gas delivery control system 31 is generally operable to control the delivery of gas to and/or from patient 11 based on various input, e.g., input received from a user (e.g., via a touch screen and/or other user interfaces provided by ventilation system 12), data received from one or more sensors 24, and/or data received from other components of ventilation system 12 (e.g., power system 30, over-pressure security system 32, exhalation valve detection system 34, and proximal pressure detection system 36). As discussed below, in some embodiments, gas delivery control system 31 may control gas delivery to patient 11 based on input from one of two sensors 24: (a) a proximal pressure sensor generally configured to measure pressure in the breathing circuit 16 near patient 11, and (b) an outlet pressure sensor generally configured to measure pressure exiting ventilation system 12 and entering breathing circuit 16.

Over-pressure security system 32 is generally operable to detect and facilitate the management of over-pressure of gas in connection system 14 (e.g., in breathing circuit 16) based on pressure signals received from one or more pressure sensors 24.

Exhalation valve detection system 34 is generally operable to determine whether an exhalation valve is present in the current configuration of system 10 (e.g., whether the currently connected breathing circuit 16 includes an exhalation valve) based on pressure signals received from one or more pressure sensors 24.

Proximal pressure detection system 36 is generally operable to determine whether proximal pressure may be measured and used by ventilation system 12 (e.g., if a proximal pressure line is properly connected and the proximal pressure sensor is working properly) based on pressure signals received from one or more pressure sensors 24.

Over-pressure security system 32, exhalation valve detection system 34, and proximal pressure detection system 36, are discussed in greater detail below with reference to FIG. 2.

Oxygen safety system 38 is generally operable to slow or stop the flow of a supplemental oxygen supply in particular circumstances, e.g., when gas delivery system 20 is not running and/or overheating. Oxygen safety system 38 is discussed in greater detail below with reference to FIGS. 4A and 4B.

Wireless notification module 44 is generally configured to communicate wireless notifications (e.g., alarms generated by control system 22) from ventilation system 12 to any suitable receiving device, e.g., a remote monitor or a mobile alarm unit carried by a user (e.g., a caretaker). In some embodiments, wireless notification module 44 may communicate to such receiving device(s) via one or more wireless repeaters, which may increase the physical range of wireless communications from ventilation system 12.

Sensor Systems

Figure 2:
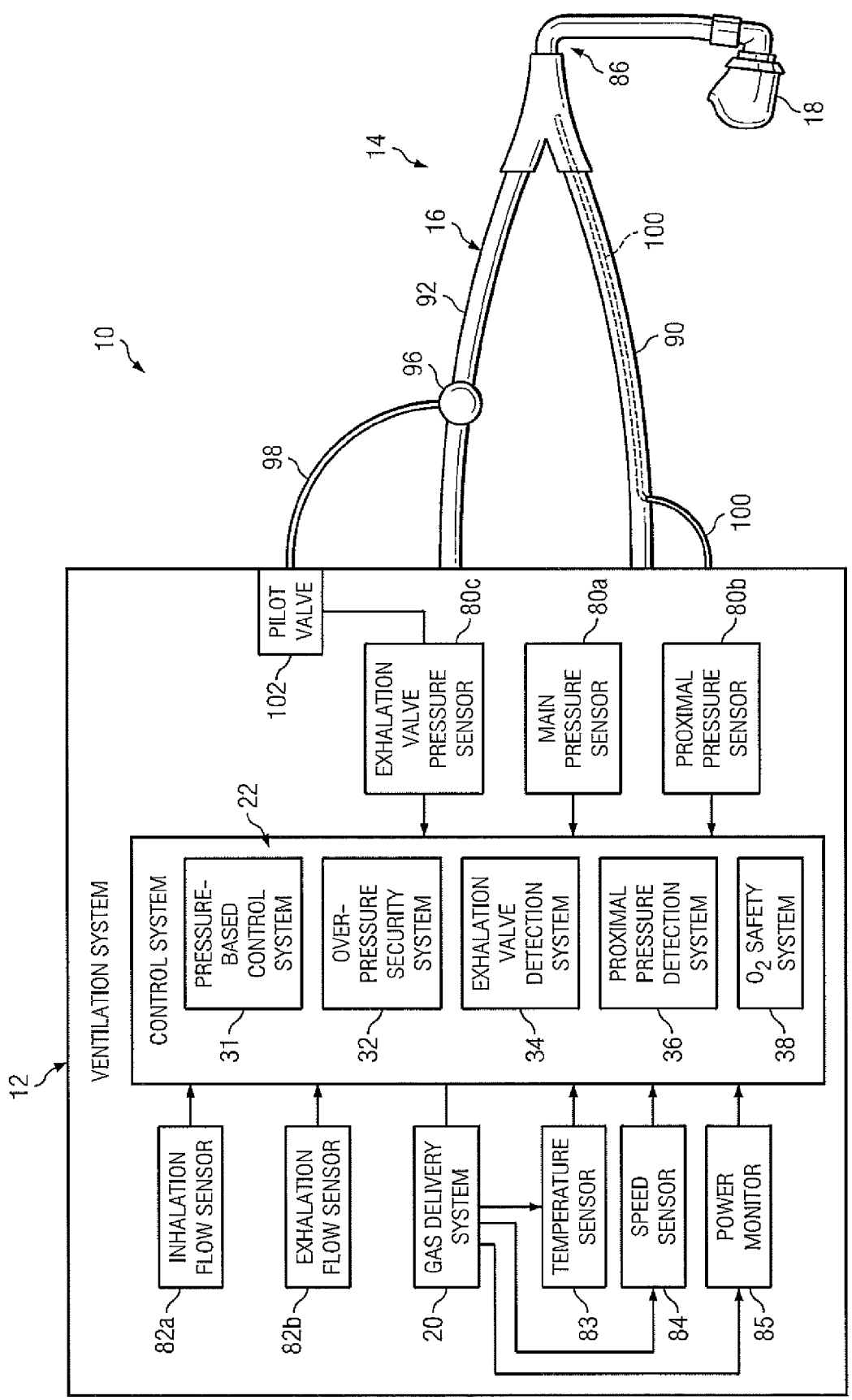
FIG. 2 illustrates an example ventilation system including an over-pressure security system, exhalation valve detection system, proximal pressure detection system, and an O2 safety system, according to certain embodiments of the present disclosure.

FIG. 2 illustrates an example ventilation system 12 including an over-pressure security system 32, exhalation valve detection system 34, proximal pressure detection system 36, and an O2 safety system 38, according to certain embodiments of the present disclosure. FIG. 2 illustrates systems 31, 32, 34, 36, and 38, various sensors 24 for providing input to systems 31, 32, 34, 36, and 38, and/or control system 22, and an example connection system 14 connected to ventilation system 12. The example connection system 14 includes a dual-limb breathing circuit 16 including an inspiratory limb 90, exhalation limb 92, exhalation valve 96, exhalation valve control line 98, and a proximal pressure line 100 running along a length of inspiratory limb 90 or exhalation limb 92.

Breathing assistance system 10 may include one or more pressure sensors 80 for providing input to systems 31, 32, 34, and 36. For example, system 10 may include any or all of the following pressure sensors:

(a) An outlet pressure sensor 80a located at or near a main gas outlet of ventilation system 12 (e.g., at or near an outlet of gas delivery system 20) to measure the pressure of gas flow exiting ventilation system 12 or gas delivery system 20, or the pressure of gas flow entering connection system 14. For example, outlet pressure sensor 80a may be located inside or just outside a housing or enclosure of ventilation system 12.

(b) A proximal pressure sensor 80b configured to measure pressure at or near the patient end of connection system 14 (indicated in FIG. 2 generally at 86), referred to as the "proximal pressure." Proximal pressure sensor 80b may be located at any suitable location. For example, proximal pressure sensor 80b may be located in ventilation system 12 and connected to a proximal pressure line 100 (e.g., a tube or other conduit) that extends along a limb 90 or 92 of breathing circuit 16 and opens near the patient end 86 of connection system 14. Thus, proximal pressure sensor 80b may measure the gas pressure at the open end (i.e., the patient end) of proximal pressure line 100. As another example, proximal pressure sensor 80b may be located at or near the open, patient end of the proximal pressure line 100 and may be configured to communicate pressure measurement signals back to ventilation system 12 (e.g., via an embedded wire in connection system 14).

Typically, the pressure measured by proximal pressure sensor 80b is lower than the pressure measured by outlet pressure sensor 80a in positive flow situations (flow toward patient 11), and greater than the pressure measured by outlet pressure sensor 80a in negative flow situations (flow away patient 11). The difference between the measurements of sensors 80a and 80b is largely or completely due to pressure drop inherent in the breathing circuit 16. Proximal pressure sensor 80b typically provides a more accurate measure of the pressure experienced by the patient, referred to as the "patient pressure."

(c) An exhalation valve pressure sensor 80c configured to measure pressure in a conduit used for controlling an exhalation valve of system 10. In some embodiments, breathing circuit 16 may include an exhalation valve 96 and an exhalation valve control line 98. Gas may be delivered from gas delivery system 20 through exhalation valve control line 98 to control exhalation valve 96. Measurements taken by exhalation valve pressure sensor 80c may be used (e.g., by control system 22) for controlling exhalation valve 96.

For example, in some embodiments, a pilot valve 102 (e.g., controlled by control system 22) may control the pressure in exhalation valve control line 98, thus controlling the operation of exhalation valve 96. Exhalation valve pressure sensor 80c may be configured to measure the pressure in exhalation valve control line 98 between the pilot valve 102 and exhalation valve 96, which measured pressure may then be used (e.g., by control system 22) for controlling the pilot valve 102 in order to control exhalation valve 96. Exhalation valve pressure sensor 80c may be located at any suitable location, e.g., within or attached to ventilation system 12 (e.g., near the pilot valve 102) or breathing circuit 16 (e.g., near exhalation valve 96).

Pilot valve 102 may comprise any type of valve operable to control gas flow through exhalation valve control line 98 in order to control exhalation valve 96. For example, pilot valve 102 may comprise a solenoid valve, a pneumatic valve, or a piezoelectric valve. In an example embodiment, pilot valve 102 is an electro valve and exhalation valve pressure sensor 80c is connected to a command port of the electro valve. In other embodiments, ventilation system 12 may not include a pilot valve.

In operation, any or all of main pressure sensor 80a, proximal pressure sensor 80b, and exhalation valve pressure sensor 80c may take and communicate pressure measurements for use by sub-systems 31, 32, 34, and/or 36 of control system 22. For example, pressure measurements taken by any or all of sensors 80a, 80b, and 80c may be communicated to control system 22 and used by the various sub-systems 31, 32, 34, and/or 36 for controlling various aspects of the operation of system 12, e.g., the delivery of gas by gas delivery system 20. Sensors 80a, 80b, and/or 80c may take and/or communicate pressure measurements according to any time schedule, e.g., periodically or substantially continuously, for example.

In addition to pressure sensors 80, breathing assistance system 10 may also include one or more flow sensors 82 for measuring gas flows and providing input to control system 22. For example, system 10 may include at least (a) an inhalation flow sensor 82a configured to measure the flow rate of gas flow delivered toward patient 11 via connection system 14, and (b) an exhalation flow sensor 82b configured to measure the flow rate of gas flow exhaled by or otherwise communicated away from patient 11 via connection system 14.

Like pressure sensors 80, each flow sensor 82 may be located at any suitable location. For example, inhalation flow sensor 82a may be located at or near a gas outlet of ventilation system 12 connected to inhalation limb 90 of breathing circuit 16, and exhalation flow sensor 82b may be located at or near a gas inlet of ventilation system 12 connected to exhalation limb 90 of breathing circuit 16.

It should be understood that ventilation system 12 includes various other components (e.g., a power system, user interfaces, a display, etc.) not shown in FIG. 2 for the sake of simplicity.

Gas Delivery Control System 31

As discussed above, gas delivery control system 31 may control the delivery of gas to and/or from patient 11 based on various input, e.g., input received from a user (e.g., via a touch screen and/or other user interfaces provided by ventilation system 12), data received from one or more sensors 24, and/or data received from other components or sub-systems of ventilation system 12. Gas delivery control system 31 may control the communication of gas to and/or from patient 11 by controlling, for example, the operation of gas delivery system 20 and/or the operation of one or more valves in order to control the pressure and/or flow rate of gas delivered to and/or communicated from patient 11.

For example, gas delivery control system 31 may regulate the pressure and/or flow rate of gas communicated to and/or from patient 11 based on pressure and/or flow data received from pressure and/or flow sensors 24. As another example, gas delivery control system 31 may shut down or reduce the pressure and/or flow rate of gas delivered to patient 11 based on signals received from over-pressure security system 32 indicating an over-pressure situation. As another example, gas delivery control system 31 may control the pressure and/or flow rate of gas communicated to and/or from patient 11 based on signals received from exhalation valve detection system 34 indicating whether or not an exhalation valve is being used in the current system configuration. As another example, gas delivery control system 31 may control the pressure and/or flow rate of gas communicated to and/or from patient 11 based on signals received from proximal pressure detection system 36 indicating whether or not a proximal pressure sensor is currently connected and operational. Example implementations of each of these techniques for controlling system 10 are discussed below.

Gas delivery control system 31 may include or have access to any instructions (e.g., any suitable software, algorithms, or other logic or instructions that may be executed by one or more processors) for automatically controlling the operation of ventilation system 12 (e.g., controlling the pressure and/or flow rate output by gas delivery system 20 and/or controlling one or more valves) based on any of the various input data discussed herein.

Gas delivery control system 31 may control gas delivery system 20 directly, or by controlling another system or device configured to control gas delivery system 20. For example, in embodiments including a turbine-based blower 20, gas delivery control system 31 may control a turbine control device 200 (e.g., see FIG. 6), which in turn controls the turbine.

In some embodiments, gas delivery control system 31 may control gas delivery to patient 11 based on input from (a) outlet pressure sensor 80a (for measuring the pressure of gas exiting ventilation system 12 or entering connection system 14) and/or (b) proximal pressure sensor 80b (for measuring the pressure of gas in connection system 14 near patient 11). For example, as discussed below in the "Dual-Sensor System and Proximal Pressure Detection" section, system 12 may default to using proximal pressure sensor 80b for controlling ventilation, but switch to outlet pressure sensor 80a as a backup when proximal pressure line 100 is not connected to system 12 or the proximal pressure cannot effectively be used for some other reason.

As another example, gas delivery control system 31 may use readings from both outlet pressure sensor 80a and proximal pressure sensor 80b for controlling ventilation. For example, control system 31 may calculate an average, or weighted average, of readings from sensor 80a and sensor 80b to determine effective pressure values for use in controlling ventilation. As another example, control system 31 may calculate effective pressure values using any other algorithm(s) incorporating readings from both sensors 80a and 80b. One example algorithm provides:

$$P_E = A^*(P_{proximal}) + B^*(P_{outlet}) \quad (1)$$

where:
$P_E$=the effective pressure that may be used for controlling ventilation;
$P_{proximal}$=pressure measured by proximal pressure sensor 80b;
$P_{outlet}$=pressure measured by outlet pressure sensor 80a; and
A and B are coefficients (e.g., positive values having a sum of 1.0).

Another example algorithm provides:

$$P_E = A^*(P_{proximal}) + B^*(P_{outlet} + P_{drop}) \quad (2)$$

where $P_{drop}$=a pressure drop compensation value. $P_{drop}$ may be an estimate of the pressure drop inherent in connection system 14 between outlet pressure sensor 80a and patient 11, which pressure drop may be a function of the flow rate through connection system 14. $P_{drop}$ may be determined in any known or suitable manner, e.g., using techniques described in co-pending EP Patent Application EP 08006240.9, filed on Mar. 31, 2008, and entitled "Systems and Methods for Compensating for Pressure Drop in a Breathing Assistance System."

Dual-Sensor System and Proximal Pressure Detection

As discussed above, proximal pressure detection system 36 may be generally operable to determine whether proximal pressure may be effectively used by ventilation system 12 (e.g., if a proximal pressure line 100 is properly connected and the proximal pressure sensor 80b is providing useful readings) based on pressure signals received from one or more pressure sensors 24.

Gas delivery control system 31 may control the pressure and/or flow of gas delivered toward patient 11 based on one or both of (a) outlet pressure measured by outlet pressure sensor 80a and (b) proximal pressure measured by proximal pressure sensor 80b. As discussed above, proximal pressure measured by proximal pressure sensor 80b typically provides a more accurate measure of the patient pressure than outlet pressure measured by outlet pressure sensor 80a. Thus, it may be desirable to use proximal pressure for controlling the pressure and/or flow of delivered gas, assuming that proximal pressure may be effectively used for controlling ventilation (e.g., if a proximal pressure line 100 is properly connected and the proximal pressure sensor 80b is working property). If proximal pressure cannot be effectively used for controlling ventilation (e.g., if a proximal pressure line 100 is not connected or is blocked, or if proximal pressure sensor 80b is not working properly), gas delivery control system 31 may use outlet pressure sensor 80a as a backup for measuring pressure for controlling ventilation; however, as such pressure measurements may be less accurate, the ventilation control may be less than optimal in certain ventilation modes or applications.

Therefore, proximal pressure detection system 36 may determine whether proximal pressure may be effectively used, e.g., by gas delivery control system 31 for controlling ventilation pressure and/or flow. Proximal pressure detection system 36 may compare measurements from outlet pressure sensor 80a with measurements from proximal pressure sensor 80b, and determine whether or not proximal pressure can be effectively used based on the results of such comparison. For example, proximal pressure detection system 36 may determine that proximal pressure can be effectively used if the outlet pressure (measured by sensor 80a) is greater than the proximal pressure (measured by sensor 80b), but not if the outlet pressure is less than or equal to the proximal pressure (during positive direction flow, i.e., toward patient 11). As another example, proximal pressure detection system 36 may determine that proximal pressure can be effectively used if the outlet pressure is greater than the proximal pressure, but not by more than a predetermined threshold value. The preceding examples assume positive direction flow (i.e., toward patient 11); for negative direction flow (i.e., away from patient 11), the analysis would be reversed.

As another example, proximal pressure detection system 36 may compare a proximal pressure measurement taken at a particular flow rate to a predetermined expected pressure value for the particular flow rate, and determine that proximal pressure can be effectively used if the measured proximal pressure does not differ from the expected pressure value by more than a predetermined threshold value.

In other embodiments, proximal pressure detection system 36 may separately determine (a) whether a proximal pressure line 100 is not connected to system 12 and (b) whether readings from proximal pressure sensor 80b are effective, or usable, and use both determinations for controlling various aspects of the operation of ventilation system 12.

Based on the results of any of such analyses discussed above, proximal pressure detection system 36 may communicate a notification to gas delivery control system 31 indicating whether proximal pressure cannot be effectively used. If proximal pressure cannot be effectively used, gas delivery control system 31 may subsequently use outlet pressures (measured by sensor 80a) for controlling ventilation, and/or may trigger an alarm or notification to the user that the proximal pressure system is not connected or not working properly. The alarm may comprise any notification that may be sensed by a user, e.g., an audible alarm or a visible alarm displayed to the user, e.g., via display 28 or separate device (e.g., an LED). If proximal pressure can be effectively used, no alarm is triggered (although gas delivery control system 31 may notify the user that proximal pressure is being used) and ventilation may begin, or continue, using proximal pressure to control ventilation pressure and/or flow.

Proximal pressure detection system 36 may determine whether or not proximal pressure can be effectively used at any suitable time. For example, system 36 may perform such analysis prior to, or during, the initiation of ventilation in order to establish the most accurate control system. In addition, system 36 may perform such analysis periodically or substantially continuously during ventilation of patient 11, e.g., such that system 36 may adjust to a disconnection (or connection) of proximal pressure line 100 during ventilation. If gas delivery control system 31 is using proximal pressure to control ventilation, and system 36 determines that proximal pressure can no longer be effectively used (e.g., upon disconnection of proximal pressure line 100 from system 12), system 36 may notify gas delivery control system 31 such that gas delivery control system 31 can switch to using outlet pressure (measured by sensor 80a) and trigger an alarm that the proximal pressure system has been disconnected or is not working properly. Similarly, if gas delivery control system 31 is using outlet pressure to control ventilation, and system 36 determines that proximal pressure can now be effectively used (e.g., upon connection of proximal pressure line 100 to system 12), system 36 may notify gas delivery control system 31 such that gas delivery control system 31 can switch to using proximal pressure (measured by sensor 80b) to control ventilation. Thus, gas delivery control system 31 can automatically switch between using outlet pressure sensor 80a and proximal pressure sensor 80b, depending on whether proximal pressure can currently be used (e.g., depending on whether a pressure line 100 is currently connected).

In addition, in some embodiments, control system 22 may allow or disallow certain ventilation modes or settings based on whether gas delivery control system 31 is currently using outlet pressure or proximal pressure to control ventilation (e.g., based on whether or not a pressure line 100 is currently connected). For example, certain ventilation modes or settings may require accurate patient pressure readings that may be provided by proximal pressure sensor 80b but not by outlet pressure sensor 80a. Thus, control system 22 may disallow user selection of, and/or automatic switching to, such ventilation modes or settings while outlet pressure is being used to control ventilation (e.g., when pressure line 100 is not connected to system 12). An alarm or notification indicating that such ventilation modes or settings are not available due to pressure line 100 not being connected may be displayed to the user, e.g., via display 28. If a pressure line 100 is then connected/re-connected to system 12, control system 22 may allow user selection or switching to such disallowed ventilation modes or settings.

In some embodiments, if proximal pressure line 100 becomes disconnected while operating according to a ventilation mode or settings that requires proximal pressure readings (from sensor 80b), proximal pressure detection system 36 may detect the disconnection and gas delivery control system 31 may automatically adjust the ventilation (e.g., by switching to a different ventilation mode or adjusting one or more settings) to be compliant with operation based on outlet pressure readings (from sensor 80a). Gas delivery control system 31 may also generate an alarm or notification to the user that the proximal pressure line is disconnected and/or that the ventilation mode or settings have been automatically changed. If proximal pressure line 100 is then re-connected while operating according to the changed ventilation mode or settings based on outlet pressure readings, proximal pressure detection system 36 may detect the re-connection and gas delivery control system 31 may automatically switch back to the previous ventilation mode or settings, or may automatically display to the user a selectable option to return to such previous ventilation mode or settings.

Proximal pressure detection system 36 may include or have access to one or more controllers, processors, memory devices, and any other suitable hardware, software, and/or firmware for providing any of the various functionality discussed herein. Such memory device(s) may store instructions (e.g., any suitable software, algorithms, or other logic or instructions that may be executed by one or more processors) for providing such functionality. Proximal pressure detection system 36 may be partially or fully integrated with, or may be distinct from, gas delivery control system 31.

Over-Pressure Security

As discussed above, over-pressure security system 32 is generally operable to detect and facilitate the management of over-pressure of gas in connection system 14 (e.g., in breathing circuit 16) based on pressure signals received from one or more pressure sensors 24. For example, over-pressure security system 32 may provide either or both of the levels of over-pressure security discussed below.

A first level of over-pressure security is based on redundancy of pressure measurements from outlet pressure sensor 80a and proximal pressure sensor 80b. As discussed above, outlet pressure sensor 80a may measure pressure at or near a main gas outlet of ventilation system 12 (i.e., the pressure of gas flow entering connection system 14), and proximal pressure sensor 80b may measure "proximal pressure" at or near the open end (i.e., the patient end) of a proximal pressure line 100 extending along a limb of breathing circuit 16. The two sensors 80a and 80b may produce different results due to pressure drop inherent in breathing circuit 16.

The first level of over-pressure security involves monitoring both outlet pressure sensor 80a and proximal pressure sensor 80b to detect an over-pressure condition in connection system 14. For example, over-pressure security system 32 may compare pressure measurements received from sensors 80a and 80b to one or more threshold pressure values to automatically detect an over-pressure condition. Pressure measurements from both sensors 80a and 80b may be compared to a single pressure threshold value, or each sensor's measurements may be compared to a separate corresponding pressure threshold value. Such pressure threshold value(s) may be determined in any suitable manner, and may vary over time.

If some embodiments, the determination of pressure threshold values depends on the selected ventilation mode and/or breath type. For example, in one embodiment:

For Volume modes, the pressure threshold value is set by a user via GUI 40 as a "high pressure" alarm threshold.

For Pressure modes, the pressure threshold value is automatically calculated on the basis of the ventilation pressure set by the user via GUI 40, e.g., according to the equation:

Pressure threshold=$P_{control}$(or $P_{support}$)+X% where:
$P_{control}$ represents the pressure setting in a Control mode;
$P_{support}$ represents the pressure setting in a Support mode; and
X is a preset coefficient, e.g., 10% or 20%.

If over-pressure security system 32 detects an over-pressure condition, system 32 may generate an over-pressure signal to gas delivery control system 31 (and/or to an alarm system) indicating details of the over-pressure condition (e.g., relevant pressure measurement(s) and threshold value(s)). In response, gas delivery control system 31 may control gas delivery system 20 in order to end the over-pressure condition, for example by reducing the pressure or flow rate produced by gas delivery system 20 (e.g., to a pressure at or just below a threshold pressure value, or to a lower pressure) or by shutting down gas delivery system 20. For example, in embodiments in which gas delivery system 20 includes a blower (e.g., a turbine-based blower), gas delivery control system 31 may reduce the speed of the blower.

Monitoring signals from both sensors 80a and 80b may provide redundancy to account for situations in which 80a or 80b is not providing useful data, e.g., where one of sensors 80a and 80b is damaged or not working properly, or where a proximal pressure line 100 is not used or is blocked.

A second level of over-pressure security is based on pressure measurements from exhalation valve pressure sensor 80c used for detecting the presence of an exhalation valve 96 and controlling the operation of such exhalation valve 96 (e.g., by generating pressure signals used to control a pilot valve 102 that controls exhalation valve 96, as discussed above). For certain exhalation valves 96, the effective surface area upon which gas pressure acts from the command side of the valve (i.e., the side facing exhalation valve control line 98) is larger than the effective surface area upon which gas pressure acts from the breathing circuit side of the valve (i.e., the side facing exhalation valve control line 98). Such configuration may provide the desired sealing of exhalation valve 96.

In normal operation, exhalation valve pressure sensor 80c may be automatically controlled to maintain an internal pressure inside exhalation valve 96 substantially equal to the pressure inside breathing circuit 16 near valve 96, based on pressure measurements from pressure sensors 80a, 80b, and/or 80c. However, in an over-pressure situation, the internal pressure inside exhalation valve 96 may be automatically maintained at a maximum setting level (e.g., an IPAP setting if operating in a barometric mode or a "high pressure" setting if operating in a volumetric mode) based at least on pressure measurements from exhalation valve pressure sensor 80c. In such situation, the pressure inside breathing circuit 16 may exceed the internal pressure inside exhalation valve 96, and exhalation valve 96 may leak, thus reducing and/or limiting the pressure in breathing circuit 16.

Thus, in embodiments or situations in which the first level of over-pressure security is not provided or not effective (e.g., where both sensors 80a and 80b fail, or where gas delivery control system 31 fails to correct an over-pressure situation), the internal pressure inside exhalation valve 96 may be limited based on measurements from exhalation valve pressure sensor 80c, providing leakage through exhalation valve 96, thus reducing and/or limiting the pressure in breathing circuit 16. In this manner, exhalation valve pressure sensor 80c may facilitate the second level of over-pressure security.

Over-pressure security system 32 may include or have access to one or more controllers, processors, memory devices, and any other suitable hardware, software, and/or firmware for providing any of the various functionality discussed herein. Such memory device(s) may store instructions (e.g., any suitable software, algorithms, or other logic or instructions that may be executed by one or more processors) for providing such functionality. Over-pressure security system 32 may be partially or fully integrated with, or may be distinct from, gas delivery control system 31.

Exhalation Valve Detection

As discussed above, exhalation valve detection system 34 is generally operable to determine whether an exhalation valve 96 is present in the current configuration of system 10 (e.g., whether the currently connected breathing circuit 16 includes an exhalation valve 96) based on pressure signals received from one or more pressure sensors 24.

In some embodiments, exhalation valve pressure sensor 80c may be used to detect whether an exhalation valve 96 is present. For example, gas may be delivered through an outlet configured for connection to an exhalation valve control line 98. If an exhalation valve control line 98 leading to an exhalation valve 96 is present, pressure in exhalation valve control line 98 increases, which increased pressure may be detected by exhalation valve pressure sensor 80c. However, if an exhalation valve control line 98 leading to an exhalation valve 96 is not present, pressure in exhalation valve control line 98 remains low, which low pressure may be detected by exhalation valve pressure sensor 80c. The pressure measured by exhalation valve pressure sensor 80c may thus be compared against an appropriate threshold value to determine whether an exhalation valve 96 is present. Such threshold value may be determined in any suitable manner, and may depend upon various factors, e.g., the current ventilation mode, a flow rate setting, or a pressure setting.

In one embodiment, exhalation valve pressure sensor 80c is connected to a command port of a pilot valve 102 (e.g., an electro valve) that controls exhalation valve 96 on breathing circuit 16 via exhalation valve control line 98. At the beginning of ventilation, pilot valve 102 opens in order to fill exhalation valve 96 via an exhalation valve control line 98 that may be connected to ventilation system 12. If an exhalation valve control line 98 with exhalation valve 96 is connected to ventilation system 12, pressure in exhalation valve control line 98 increases, which is detected by sensor 80c. However, if an exhalation valve control line 98 with exhalation valve 96 is not connected to ventilation system 12, pressure in exhalation valve control line 98 remains low, which is detected by sensor 80c.

Exhalation valve detection system 34 may communicate a notification to gas delivery control system 31 indicating whether system 10 includes an exhalation valve 96. Gas delivery control system 31 may automatically select between different ventilation styles or modes or otherwise control one or more ventilation parameters (e.g., flow and/or pressure) based on such notification, e.g., by controlling gas delivery system 20.

For example, in some embodiments, ventilation system 12 can provide either leakage ventilation or exhalation valve ventilation. Gas delivery control system 31 may automatically control ventilation parameters (e.g., ventilation flow and pressure) to provide either leakage ventilation or exhalation valve ventilation, based on whether or not system 10 includes an exhalation valve 96. If system 10 includes an exhalation valve 96 (e.g., a dual-limb breathing circuit 16 is connected to system 12), gas delivery control system 31 may automatically adapt to provide exhalation valve ventilation; alternatively, if system 10 does not include an exhalation valve 96 (e.g., a single-limb breathing circuit 16 is connected to system 12), gas delivery control system 31 may automatically adapt to provide leakage ventilation. However, if selected ventilator settings or ventilation mode are incompatible with the relevant ventilation type (leakage ventilation or exhalation valve ventilation), gas delivery control system 31 may trigger an alarm and wait for the user to adjust the selected settings to become compatible before beginning ventilation of patient 11. The alarm may comprise any notification that may be sensed by a user, e.g., an audible alarm or a visible alarm displayed to the user, e.g., via display 28 or separate device (e.g., an LED).

Exhalation valve detection system 34 may include or have access to one or more controllers, processors, memory devices, and any other suitable hardware, software, and/or firmware for providing any of the various functionality discussed herein. Such memory device(s) may store instructions (e.g., any suitable software, algorithms, or other logic or instructions that may be executed by one or more processors) for providing such functionality. Exhalation valve detection system 34 may be partially or fully integrated with, or may be distinct from, gas delivery control system 31.

Power System/Battery

Figure 3:
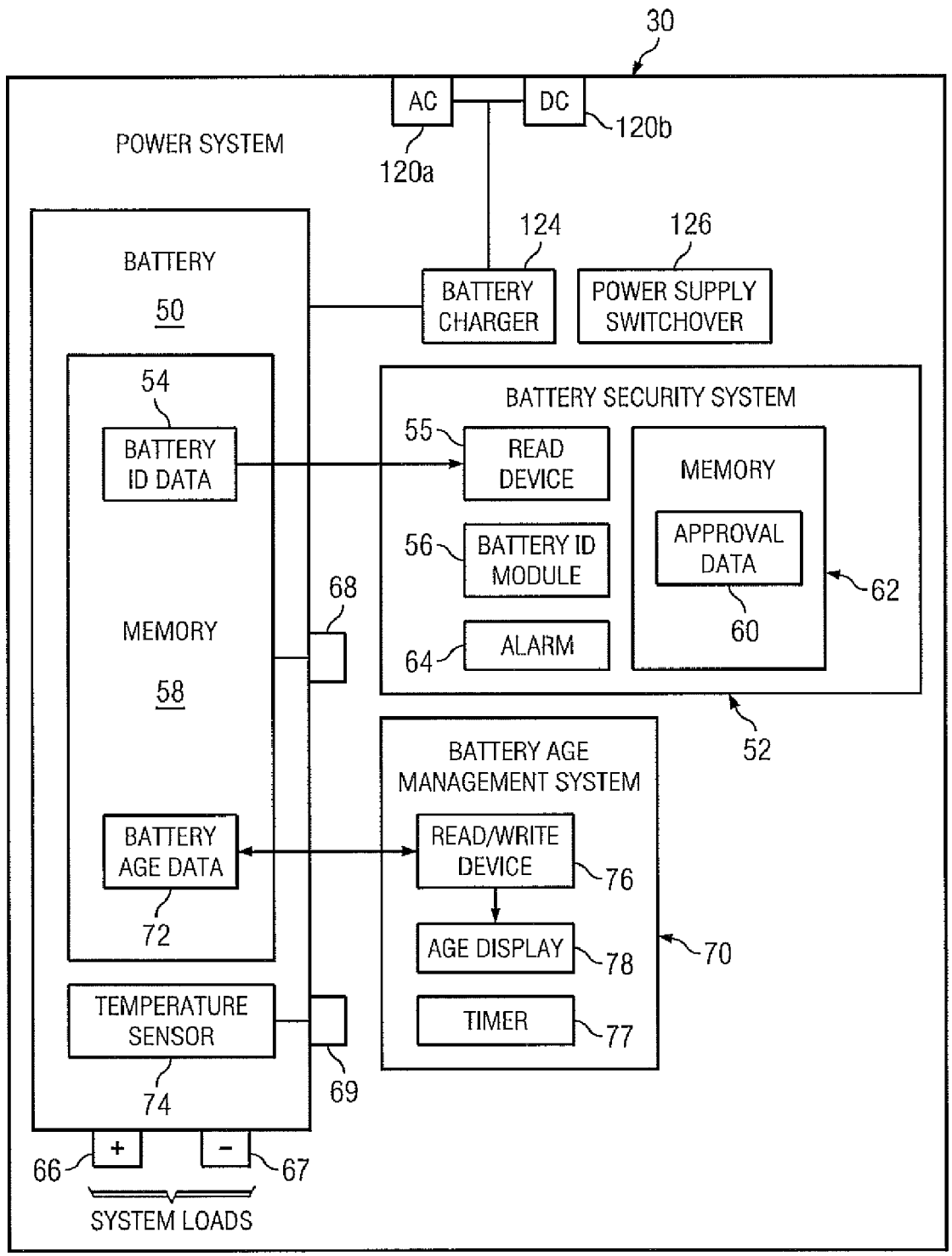
FIG. 3 illustrates details of an example power system for a ventilation system, according to certain embodiments of the present disclosure.

FIG. 3 illustrates details of an example power system 30 for ventilation system 12, according to certain embodiments of the present disclosure. Power system 30 may include or facilitate the connection of one or more sources of power for ventilation system 12, such as an external AC power source, an external DC power source, and/or one or more rechargeable batteries 50, for example. In some embodiments, power system 30 may include one or more converters 124 (e.g., a DC/DC converter and/or an AC/DC converter). One or more power sources may be removable from ventilation system 12. For example, an AC or DC power source or may be plugged into and/or unplugged from ventilation system 12 via one or more power source connections 120. As another example, one or more rechargeable batteries 50 may be inserted into and/or removed from ventilation system 12. In some embodiments, ventilation system 12 may be configured for one or more "swappable" or "hot swappable" batteries 50. In the example embodiment discussed below with reference to FIG. 6, power system 30 may include a lithium battery 50, a connection 120a for an external 110/220V AC power source, a connection 120b for an external 24V DC power source, a battery charger 124, and a power supply switchover 126 for switching between the battery 50 and an external AC or DC power source.

In some embodiments including a battery 50, power system 30 may include a battery security system 52 for ensuring that only compliant or authorized batteries may be used in ventilation system 12 and/or a battery age management system 70 for recording and displaying age data regarding a battery 50, e.g., the number of charge and discharge cycles the battery 50 has experienced.

Battery security system 52 may include a data read device 55, a battery identification module 56, and approval data 60 stored in memory 62 or otherwise accessible by battery identification module 56. Battery security system 52 is generally operable to read battery identification data 54 from battery 50 and determine, based on such data 54, whether battery 50 is approved for use in ventilation system 12. For example, battery security system 52 may compare battery identification data 54 read from a battery 50 with approval data 60 to determine whether the battery 50 is approved.

Battery identification data 54 may be stored in battery 50 (e.g., stored in memory), marked on battery 50 (e.g., a scanable bar code), or otherwise associated with battery 50. In some embodiments, battery identification data 54 may be stored in memory 58 in battery 50. Memory 58 may comprise any type of tangible memory device configured to store electronic data (e.g., RAM, DRAM, ROM, EPROM, Flash memory, or any other memory or storage device). In an example embodiment, memory 58 may comprise a single pin memory configuration such that read and write operations occur through the same pin.

Battery identification data 54 may include any data that may be used for determining whether battery 50 is compliant or authorized, e.g., a product ID number, data identifying the battery manufacturer, data identifying production data (e.g., a date code), data identifying the battery type, data identifying the storage capacity, etc. Battery identification data 54 may or may not be encrypted. In particular embodiments, battery identification data 54 is not encrypted such that neither battery 50 nor system 12 includes encoders and/or decoders for such data.

Approval data 60 may include, for example, approved product ID numbers, approved battery manufacturer(s), approved production data (e.g., approved date codes), approved battery type(s), and/or approved storage capacity(ies). Approval data may be stored in memory 62, which may comprise any type of tangible memory device configured to store electronic data (e.g., RAM, DRAM, ROM, EPROM, Flash memory, or any other memory or storage device).

Data read device 55 may comprise any device configured to read data from battery 50. In particular, data read device 55 may read battery identification data 54 from memory 58 in battery 50.

Battery identification module 56 is generally operable to determine, based on battery identification data 54 read by data read device 55, whether battery 50 is compliant or authorized for use in ventilation system 12. For example, battery identification module 56 may compare battery identification data 54 read from battery 50 with approval data 60 to determine whether the battery 50 is approved.

If battery identification module 56 determines, based on battery identification data 54 read from a battery 50 and/or approval data 60, that a battery 50 inserted in ventilation system 12 is compliant or authorized, module 56 will allow the battery 50 to provide power to system 12 and not trigger an alarm. However, if battery identification module 56 determines that a battery 50 inserted in ventilation system 12 is not compliant or not authorized, module 56 may prevent battery 50 from providing power to system 12 and/or may generate a signal to trigger an alarm 64 to notify the user to remove the non-compliant/unauthorized battery. Alarm 64 may comprise any notification that may be sensed by a user, e.g., audible alarm or a visible alarm displayed to the user. A visible alarm may be displayed in any suitable manner, e.g., an image or text displayed on display 28 or an LED or other light or visible device separate from display 28.

Battery security system 52 may perform such battery authorization process discussed above at any suitable time(s), e.g., upon a triggering event, such as the insertion of battery 50 into system 12 or system 12 being turned on, or in response to a manual user request to check the battery. In some embodiments, battery security system 52 may also automatically perform the battery authorization process periodically, e.g., every hour.

As discussed above, power system 30 may include a battery age management system 70 for recording and displaying age data regarding a battery 50. Battery age management system 70 may include a data read/write device 76 configured to write data to and/or read data from memory 58, including battery age data 72. Battery age data 72 may be stored in memory 58. In alternative embodiments, battery age data 72 and battery identification data 54 may be stored in separate memory devices in battery 50.

Battery age data 72 may include any data regarding the age or usage of a battery 50, e.g., the usage time (e.g., total hours of use), the total number of charge/discharge cycles the battery 50 has experienced, the usage time since the last charge, the effective usage time for the previous charge before needing recharge, etc.

Battery age data 72 may be stored and/or updated in memory 58 in battery 50 in any suitable manner. For example, data read/write device 76 may write battery age data 72 to memory 58 and/or update battery age data 72 stored in memory 58. Updating battery age data 72 may include storing updated data over existing stored data, or storing updated data in addition to existing stored data. Data read/write device 76 may write any type of battery age data 72 to memory 58. Data read/write device 76 may write such data at any suitable time, e.g., periodically or upon a triggering event, such as the beginning or completion of a charge or discharge of battery 50, ventilation system 12 being turned on or off, or ventilation system 12 being plugged into or unplugged from an external power source. Data read/write device 76 may include or have access to a clock or timer 77.

Data read/write device 76 may also read any type of battery age data 72 from memory 58 in battery 50. Data read/write device 76 may read such data at any suitable time, e.g., periodically or upon a triggering event, such as the beginning or completion of a charge or discharge of battery 50, ventilation system 12 being turned on or off, ventilation system 12 being plugged into or unplugged from an external power source, or in response to a user request.

Data read/write device 76 may be configured to display or generate signals for displaying any type of battery age data 72 from memory 58. For example, data read/write device 76 may be generate signals for displaying the total number of charge/discharge cycles the battery 50 has experienced on display 28. In an example embodiment, GUI 40 provides a user interface for accessing various types of battery age data 72 (e.g., using buttons, menus, or other interfaces for selecting the desired battery age data 72).

In other embodiments, battery 50 itself may include processing resources, software or firmware, and/or a clock or timer configured to store and/or update battery age data 72 in memory 50. For example, battery 50 may use such resources to generate and store/update any type of battery age data 72 in memory 50 periodically or upon a triggering event, e.g., the beginning or completion of a charge or discharge of battery 50, ventilation system 12 being turned on or of, or ventilation system 12 being plugged into or unplugged from an external power source. Such triggering events may be detected by battery 50 itself, or via signals communicated from battery age management system 70.

Battery 50 may also include a temperature sensor 74 for monitoring the temperature of battery 50. In some embodiments, temperature sensor 74 is not electrically connected to memory 58.

As shown in FIG. 3, battery 50 may have four contacts: (1) a positive terminal 66, (2) a negative terminal 67, (3) a memory contact 68, and (4) a temperature sensor contact 69. Positive and negative terminals 66, 67 are connected to circuitry within system 12 to provide power to system loads. Memory contact 68 may be connected to data read device 55 of battery security system 52 and/or data read/write device 76 of battery age management system 70, allowing read device 55 and/or data read/write device 76 to communicate data (e.g., battery ID data 54 and/or battery age data 72) to/from memory 58. Temperature sensor contact 69 may provide an interface for communicating battery temperature measurements to one or more components of system 12, e.g., a security system configured to determine whether battery 50 is overheating and respond accordingly.

$O_2$ Safety System $O_2$ safety system 38 is generally configured to slow or stop supplemental oxygen flow when gas delivery system 20 (e.g., a blower) is overheating and/or not running properly. $O_2$ safety system 38 may receive signals from one or more of (a) a temperature sensor 83 configured to measure a temperature of gas delivery system 20 (e.g., a blower); (b) a speed sensor 84 configured to measure an operational speed of a component (e.g., a motor, blower, turbine) of gas delivery system 20; and/or (c) a power monitor 85 configured to measure the power drawn by a component (e.g., a motor, blower, turbine) of gas delivery system 20. If $O_2$ safety system 38 determines an overheat or a danger condition, $O_2$ safety system 38 may generate a command to close an $O_2$ shut-off valve (e.g., O2 safety valve shown in FIGS. 4A, 4B, and 5) to slow or stop the flow of supplemental oxygen.

Figure 4A:
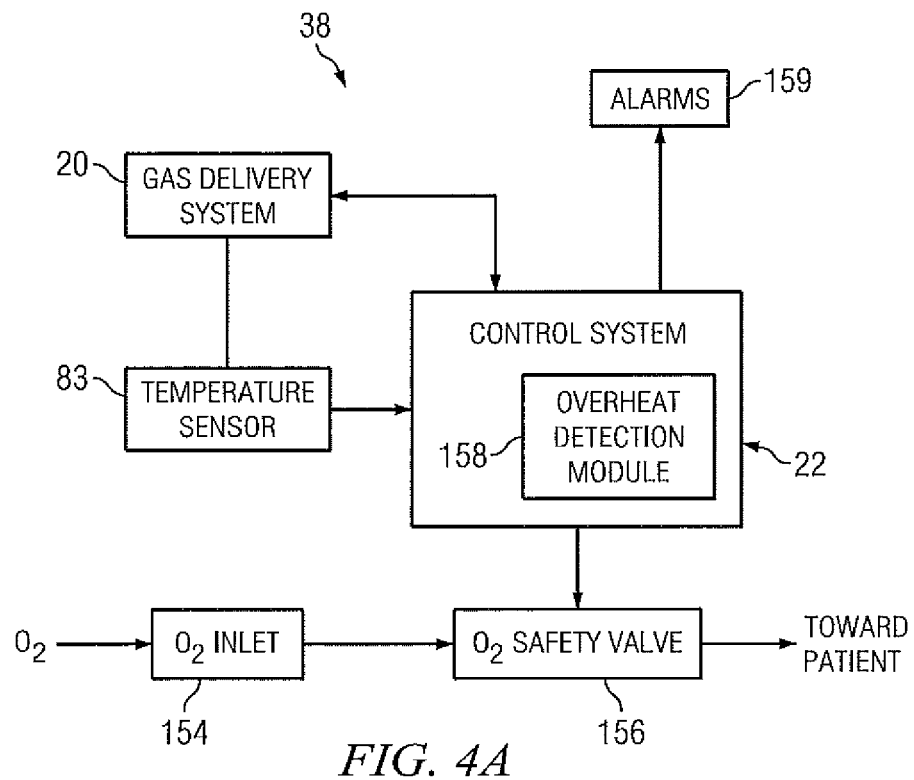
FIGS. 4A and 4B illustrate example $O_2$ safety systems for use with a ventilation system, according to certain embodiments of the present disclosure.
Figure 4B:
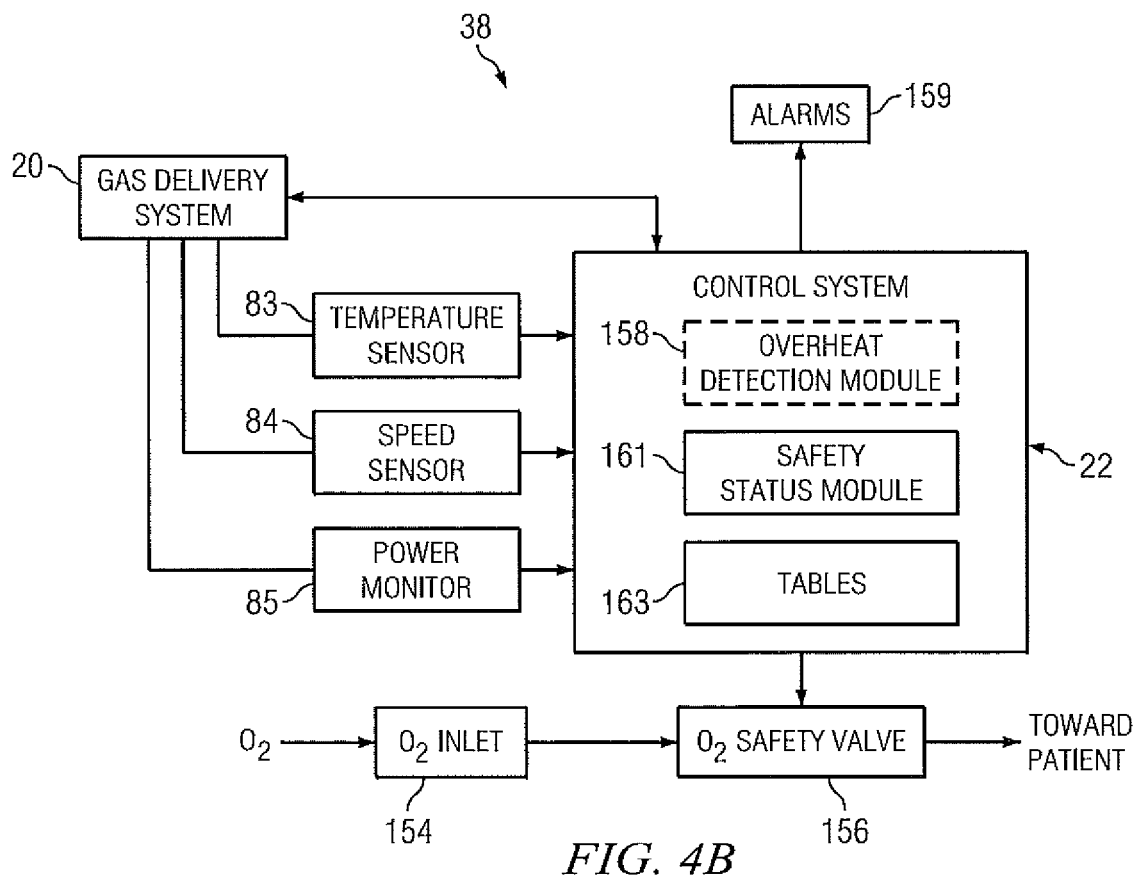

FIGS. 4A and 4B illustrate an example $O_2$ safety system 38 for use with ventilation system 12, according to certain embodiments of the present disclosure. As discussed above, $O_2$ safety system 38 is generally configured to slow or stop a supplemental oxygen flow when gas delivery system 20 (e.g., a blower) is overheating and/or not running properly. As used herein, supplemental oxygen refers to any oxygen-rich gas used to supplement the main gas flow (e.g., air) delivered to a patient 11. For example, supplemental oxygen may include pure oxygen or any other gas having an oxygen concentration greater than air. As used herein, reference to slowing or stopping a supplemental oxygen flow may refer to slowing or stopping the flow of supplemental oxygen from the supplemental oxygen supply (e.g., a tank, a concentrator, or a line from the wall) to the patient 11. For example, slowing or stopping a supplemental oxygen flow may refer to slowing or stopping a flow of supplemental oxygen into ventilation system 12 via a supplemental oxygen inlet (e.g., $O_2$ inlet 154) or through a valve of ventilation system 12 (e.g., $O_2$ safety valve 156). As another example, slowing or stopping a supplemental oxygen flow may refer to opening a release or vent valve to allow supplemental oxygen to flow out and/or away from ventilation system 12.

FIG. 4A illustrates an example $O_2$ safety system 38 in which the supplemental oxygen flow may be controlled based on temperature measurements, e.g., to slow or stop the supplemental oxygen flow in the event of an detected overheat condition. As shown in FIG. 4A, $O_2$ safety system 38 may include a temperature sensor 83, an overheat detection module 158, an O2 safety valve 156, and/or logic associated with gas delivery control system 31.

Temperature sensor 83 is configured to measure the temperature of one or more components of gas delivery system 20 (e.g., a component of a turbine-based blower). Temperature sensor 83 may take temperature measurements at any suitable time and/or frequency, e.g., substantially continuously, periodically (e.g., every 30 seconds), or in response to an event (e.g., a request received from a user).

Overheat detection module 158 is generally configured to determine whether gas delivery system 20 is overheating by monitoring readings from temperature sensor 83. For example, overheat detection module 158 may compare readings from temperature sensor 83 with threshold temperature(s) to determine whether gas delivery system 20 is overheating. Such threshold temperature(s) may be constant or may change over time. For example, a threshold temperature may be determined using an algorithm or look-tip table relating the threshold value to one or more other parameters, e.g., the current pressure or flow rate of gas delivered by delivery system 20, or the current speed of a turbine (in embodiments in which gas delivery system 20 comprises a turbine-based blower). Thus, for example, an algorithm may be used to increase the threshold temperature in proportion to the flow rate or turbine speed, as higher temperatures are expected with higher flow rates or turbine speeds.

As another example, different threshold temperatures may be used for different ventilation modes or conditions. For example, different threshold temperatures may be used for SIMV ventilation, Assist/Control ventilation, and CPAP ventilation. As another example, different threshold temperatures may be used for adult vs. pediatric ventilation, as higher temperatures are expected with adult ventilation (e.g., due to higher flow rates or turbine speeds).

Threshold temperatures may be pre-programmed into overheat detection module 158 and/or gas delivery control system 31. Alternatively, threshold temperatures may be set or modified by a user, e.g., an authorized technician. Threshold temperatures may be determined based on empirical data, data regarding various system components (e.g., a maximum temperature that a blower motor can support), based on industry regulations, or determined in any other suitable manner.

In some embodiments, overheat detection module 158 may determine two different overheat levels based on different threshold temperatures—a first overheat level that triggers control of O2 safety valve and a second overheat level that triggers control of gas delivery system 20. The first overheat level may be lower than, higher than, or the same as the second overheat level. For example, overheat detection module 158 may determine a first overheat level (for triggering control of O2 safety valve) if the measured temperature exceeds a first threshold temperature $T_1$, and a second overheat level (for triggering control of gas delivery system 20) if the measured temperature exceeds a second threshold temperature $T_2$, where $T_2 > T_1$. Thus, while operating between $T_1$ and $T_2$, gas delivery system 20 may continue to ventilate patient 11 after O2 safety valve has been closed to slow or stop the flow of supplemental oxygen.

In some embodiments, overheat detection module 158 may determine additional overheat levels for triggering control of different components of system 10 based on various threshold temperatures. Each threshold temperature $T_1$, $T_2$, etc. may be determined in any suitable manner, e.g., as discussed above.

Overheat detection module 158 may determine that gas delivery system 20 is overheating based on any number of readings from temperature sensor 83. For example, overheat detection module 158 may determine an overheat condition in response to a single sensor reading above the relevant threshold temperature. As another example, overheat detection module 158 may determine an overheat condition based on a predetermined number (e.g., 5) of consecutive sensor readings above the relevant threshold temperature, based on sensor readings remaining above the relevant threshold temperature for a predetermined duration (e.g., 10 seconds). As another example, overheat detection module 158 may determine an overheat condition based on an average of sensor readings for a predetermined number of readings or over a predetermined duration.

In response to determining an overheat condition in gas delivery system 20, overheat detection module 158 may send an overheat notification signal to gas delivery control system 31. Based on such signal, gas delivery control system 31 may control O2 safety valve and/or gas delivery system 20 accordingly. For example, gas delivery control system 31 may partially or fully close O2 safety valve to slow or stop the flow of supplemental oxygen. O2 safety valve may comprise any suitable type of valve. O2 safety valve may be separate from, or integrated with, $O_2$ inlet 154.

In addition, in some embodiments, gas delivery control system 31 may control gas delivery system 20 in response to an overheat condition. For example, where gas delivery system 20 includes a blower, gas delivery control system 31 may slow or stop the blower in order to reduce the temperature of gas delivery system 20.

In some embodiments, gas delivery control system 31 may control both O2 safety valve and gas delivery system 20 based on a single overheat notification signal. In embodiments using a first overheat level for triggering control of O2 safety valve and a second overheat level for triggering control of gas delivery system 20, gas delivery control system 31 may control O2 safety valve and gas delivery system 20 separately according to the relevant overheat signals received from overheat detection module 158.

In some embodiments, gas delivery control system 31 may control (e.g., close) O2 safety valve based on either of the following input: (a) an overheat notification signal from overheat detection module 158 or (b) a notification of an event regarding gas delivery system 20, e.g., that gas delivery system 20 is not delivering gas (e.g., turned off or in standby mode) or is not operating properly. Thus, for example, the flow of supplemental oxygen may be slowed or stopped if gas delivery system 20 is overheating, turned off, in standby mode, or not operating properly.

Overheat detection module 158 and/or gas delivery control system 31 may generate any suitable alarm(s) 159 regarding overheat conditions and/or the closing of O2 safety valve to slow or stop the flow of supplemental oxygen. An alarm 159 may comprise any notification that may be sensed by a user, e.g., audible alarm or a visible alarm displayed to the user. A visible alarm may be displayed in any suitable manner, e.g., an image or text displayed on display 28 or an LED or other light or visible device separate from display 28.

Overheat detection module 158 may include or have access to one or more controllers, processors, memory devices, and any other suitable hardware, software, and/or firmware for providing any of the various functionality discussed herein. Such memory device(s) may store instructions (e.g., any suitable software, algorithms, or other logic or instructions that may be executed by one or more processors) for providing such functionality. Overheat detection module 158 may be partially or fully integrated with, or may be distinct from, gas delivery control system 31.

FIG. 4B illustrates an example $O_2$ safety system 38 in which the supplemental oxygen flow may be controlled based on any combination of temperature measurements, speed measurements related to gas delivery system 20 (e.g., the speed of a blower motor), and the power drawn by gas delivery system 20 (e.g., the power drawn by a blower motor). The $O_2$ safety system 38 of FIG. 4B may be particularly suitable for embodiments of ventilation system 12 in which gas delivery system 20 includes a motor, e.g., for a blower or turbine As shown in FIG. 4B, $O_2$ safety system 38 may include a temperature sensor 83, a speed sensor 84, a power monitor 85, a safety status module 161, an $O_2$ safety valve 156, and/or logic associated with gas delivery control system 31.

Temperature sensor 83 is generally discussed above regarding FIG. 4A. Speed sensor 84 may comprise any system or device configured to measure an operational speed of a motor, blower, turbine, or other component of gas delivery system 20. Power monitor 85 may comprise any system or device configured to measure the power drawn by a motor, blower, turbine, or other component of gas delivery system 20.

Safety status module 161 is generally configured to analyze the operational safety status of gas delivery system 20, including determining conditions regarding gas delivery system 20 (e.g., overheating of a blower motor) that call for controlling $O_2$ safety valve 156. Such conditions are referred to herein as "danger conditions." Safety status module 161 may analyze the operational safety status of gas delivery system 20, including determining danger conditions, based on any combination of some or all of the following types of data, referred to herein as "$O_2$ safety data":

(a) temperature measurements at one or more locations of ventilation system 12;

(b) speed measurements related to gas delivery system 20 (e.g., the speed of a blower motor, fan, or turbine); and/or (c) measurements of the power drawn by gas delivery system 20 or certain component(s) thereof (e.g., the power drawn by a blower motor).

In some embodiments, safety status module 161 may calculate a safety factor using one or more algorithms relating different types of measured $O_2$ safety data, and compare the calculated safety factor to a danger condition threshold value to determine whether a danger condition is present.

In other embodiments, safety status module 161 may access look-up tables 163 relating different types of measured $O_2$ safety data to determine whether a danger condition is present. For example, for an embodiment using temperature measurements and speed measurements as $O_2$ safety data, look-up tables 163 may include a table indicating whether a danger condition is present for various combinations of temperature measurements and speed measurements.

As another example, for an embodiment using temperature measurements and power measurements as $O_2$ safety data, look-up tables 163 may include a table indicating whether a danger condition is present for various combinations of temperature measurements and power measurements.

As another example, for an embodiment using speed measurements and power measurements as $O_2$ safety data, look-up tables 163 may include tables indicating whether a danger condition is present for various combinations of speed measurements and power measurements.

As another example, for an embodiment using temperature measurements, speed measurements, and power measurements as $O_2$ safety data, look-up tables 163 may include tables indicating whether a danger condition is present for various combinations of temperature measurements, speed measurements, and power measurements.

Look-up tables 163 may be stored in any suitable storage medium associated with ventilation system 12. Look-up tables 163 may be generated in any suitable manner, e.g., using mathematical algorithms or based on empirical testing.

In other embodiments, safety status module 161 may determine whether a danger condition is present by comparing individual types of $O_2$ safety data to corresponding threshold values. In some embodiments, the danger condition determination may include a series of two or more threshold comparisons.

For example, for an embodiment using temperature measurements and speed measurements as $O_2$ safety data, safety status module 161 may identify a danger condition where (a) a current temperature measurement surpasses (e.g., is higher than) a temperature threshold value and (b) a current speed measurement surpasses (e.g., is lower than) a speed threshold value.

As another example, for an embodiment using temperature measurements and power measurements as $O_2$ safety data, safety status module 161 may identify a danger condition where (a) a current temperature measurement surpasses a temperature threshold value and (b) a current power measurement surpasses a power threshold value.

As another example, for an embodiment using speed measurements and power measurements as $O_2$ safety data, safety status module 161 may identify a danger condition where (a) a current speed measurement surpasses (e.g., is lower than) a speed threshold value and (b) a current power measurement surpasses (e.g., is higher than) a power threshold value.

As another example, for an embodiment using temperature measurements, speed measurements, and power measurements as $O_2$ safety data, safety status module 161 may identify a danger condition where (a) a current temperature measurement surpasses a temperature threshold value, (b) a current speed measurement surpasses a speed threshold value, and (e) a current power measurement surpasses a power threshold value.

As used herein, the term "surpassed" may refer to a measurement rising above a threshold value or to a measurement falling below a threshold value, depending on the particular embodiment and the particular setting for the threshold value. For example, in certain applications, a motor speed threshold value of 1,000 rpm may be surpassed when the motor speed increases above 1,000 rpm, while in other applications the motor speed threshold value may be surpassed when the motor speed falls below 1,000 rpm.

Each of the threshold values used by safety status module 161 (e.g., temperature threshold values, speed threshold values, and/or power threshold values) may be determined in any suitable manner and may be constant or may change over time. For example, a particular threshold value may be determined using an algorithm or look-up table relating the threshold value to one or more other parameters, e.g., the current pressure or flow rate of gas delivered by delivery system 20, or the current speed of a turbine (in embodiments in which gas delivery system 20 comprises a turbine-based blower).

As another example, different threshold values may be used for different ventilation modes or conditions. For example, different threshold values may be used for SIMV ventilation, Assist/Control ventilation, and CPAP ventilation. As another example, different threshold values may be used for adult vs. pediatric ventilation, as higher temperatures are expected with adult ventilation (e.g., due to higher flow rates or turbine speeds).

One or more threshold values may be pre-programmed into overheat detection module 158 and/or gas delivery control system 31. Alternatively, one or more threshold values may be set or modified by a user, e.g., an authorized technician. One or more threshold values may be determined based on empirical data, data regarding material properties of various system components, based on industry regulations, or determined in any other suitable manner.

In embodiments in which safety status module 161 compares temperature measurements to a temperature threshold value, safety status module 161 may cooperate with an overheat detection module 158, which may provide any of the functionality discussed above with respect to FIG. 4A, e.g., using different threshold temperatures for determining different overheat levels for triggering control of different components of system 10 based on various threshold temperatures.

Safety status module 161 may identify a danger condition based on any number of readings from temperature sensor 83, speed sensor 84, and/or power monitor 85. For example, in an embodiment using temperature sensor 83 and speed sensor 84, safety status module 161 may identify a danger condition based on a single reading from each of temperature sensor 83 and speed sensor 84. As another example, safety status module 161 may identify a danger condition based on a predetermined number (e.g., 5) of consecutive readings from sensors 83 and 84 indicate a danger condition, or where consecutive sensor readings indicate a danger condition for more than a predetermined duration (e.g., 10 seconds), or where an average of sensor readings for a predetermined number of readings or over a predetermined duration indicate a danger condition.

In response to determining a danger condition in gas delivery system 20, safety status module 161 may send a danger condition notification signal to gas delivery control system 31. Based on such signal, gas delivery control system 31 may control O2 safety valve and/or gas delivery system 20 accordingly. For example, gas delivery control system 31 may partially or fully close O2 safety valve to slow or stop the flow of supplemental oxygen. O2 safety valve may comprise any suitable type of valve. O2 safety valve may be separate from, or integrated with, $O_2$ in let 154.

In addition, in some embodiments, gas delivery control system 31 may control gas delivery system 20 in response to a danger condition. For example, where gas delivery system 20 includes a blower, gas delivery control system 31 may slow or stop the blower in order to reduce the temperature of gas delivery system 20.

In some embodiments, gas delivery control system 31 may control both O2 safety valve and gas delivery system 20 based on a single danger condition notification signal. In some embodiments, gas delivery control system 31 may control O2 safety valve and gas delivery system 20 separately according to different danger condition threshold levels.

In some embodiments, gas delivery control system 31 may control (e.g., close) O2 safety valve based on either of the following input: (a) a danger condition notification signal from safety status module 161 or (b) a notification of an event regarding gas delivery system 20, e.g., that gas delivery system 20 is not delivering gas (e.g., turned off or in standby mode) or is not operating properly. Thus, for example, the flow of supplemental oxygen may be slowed or stopped if gas delivery system 20 is overheating, turned off, in standby mode, or not operating properly.

Safety status module 161 and/or gas delivery control system 31 may generate any suitable alarm(s) 159 regarding danger conditions and/or the closing of O2 safety valve to slow or stop the flow of supplemental oxygen. An alarm 159 may comprise any notification that may be sensed by a user, e.g., audible alarm or a visible alarm displayed to the user. A visible alarm may be displayed in any suitable manner, e.g., an image or text displayed on display 28 or an LED or other light or visible device separate from display 28.

Safety status module 161 may include or have access to one or more controllers, processors, memory devices, and any other suitable hardware, software, and/or firmware for providing any of the various functionality discussed herein. Such memory device(s) may store instructions (e.g., any suitable software, algorithms, or other logic or instructions that may be executed by one or more processors) for providing such functionality. Safety status module 161 may be partially or fully integrated with, or may be distinct from, gas delivery control system 31.

Although the discussion herein focuses on safety systems for a supplemental supply of oxygen, the various techniques discussed herein may similarly be used for providing a safety system for a supply of any other type of gas or gas mixture (e.g., an oxygen-rich mixture).

Example Ventilation Systems

FIG. 5 illustrates a flow path diagram showing various components and gas flow paths in an example embodiment of ventilation system 12, indicated as ventilation system 12*a*, according to one embodiment of the present disclosure. The particular set of components, and arrangement of such components, shown in ventilation system 12*a* represent only an example embodiment ventilation system 12; in other embodiments ventilation system 12 may include different components and/or a different arrangement of components.

An example dual-limb breathing circuit 16 is shown connected to ventilation system 12*a*. However, a different type of dual-limb breathing circuit, or a single-limb breathing circuit, may be connected to ventilation system 12*a*.

Ventilation system 12*a* provides a first flow path for air flow and a second, optional flow path for supplemental oxygen. Air flow path may include an air inlet filter 140, an inlet silencer 150, a turbine-based blower 20, and an outlet silencer 152. Air inlet filter 140 may be any filter suitable for filtering or cleaning air before entering turbine 20. For example, air inlet filter 140 may comprise a double material filter, e.g., including a fine particulate portion and a rough foam portion. Turbine 20 may comprise a high-speed, low-inertia air compressor configured to control the air flow and/or pressure through the mainstream pathway toward inspiration flow outlet 130. Silencers 150 and 152 may comprise any noise devices for suppressing noise firm the inlet or outlet interfaces of turbine 20. For example, silencers 150 and 152 may comprise any suitable materials that provide noise damping, absorbing, and/or insulating, e.g., foams and other materials such as those provided by PINTA ENAC S.A.S. (http://www.pinta-enac.com/index_eng.html). In addition, such foams or other noise controlling materials may be configured to form a labyrinth or other convoluted or tortuous path to provide additional noise control.

The supplemental oxygen flow path may include an O2 inlet 154 and an O2 safety valve, after which the path may combine with the air flow path at a union 128. Oxygen inlet 154 may comprise a low-pressure oxygen inlet interface for connecting to a supplemental oxygen source (e.g., a tank, compressor, or line-in from a wall). It may include a safety coupling valve for preventing leakage during disconnection of the oxygen source. O2 safety valve may close oxygen inlet 154 when ventilation system 12*a* is turned off or otherwise not providing ventilation, e.g., as discussed above regarding O2 safety system 38.

The combined paths may then continue toward an inspiration flow outlet 130, to which an inspiration limb 90 of breathing circuit 16 may be connected. An over-pressure pressure relief valve 160, an inspiration flow sensor 82*a*, and an outlet pressure sensor 80*a* may be connected between union 128 and inspiration flow outlet 130. Over-pressure pressure relief valve 160 may comprise any known pressure relief valve. Relief valve 160 may be configured to protect the patient from dangerous over-pressure situations. Other embodiments may not include relief valve 160, and may utilize an over-pressure safety system using pressure measurements from sensors 80*a* and/or 80*b* and gas delivery control system 31 to control turbine 20, e.g., as discussed above regarding over-pressure security system 32. Flow sensor 82*a* may monitor the flow delivered toward the patient, and outlet pressure sensor 80*a* may monitor the pressure at the outlet of ventilation system 12*a*, e.g., to provide safety back-up pressure measurement when proximal pressure line 100 is not connected.

An exhalation limb 90 of breathing circuit 16 may be connected to an exhalation flow inlet 132, which may be directed toward an exhalation flow outlet 134 leading out of ventilation system 12*a*. An exhalation flow sensor 82*b* may be located between exhalation flow inlet 132 and exhalation flow outlet 134 to measure the exhalation flow.

Ventilation system 12*a* may also include an exhalation valve control system for controlling exhalation valve 96. Such exhalation valve control system may include a pilot valve 102 and an exhalation valve pressure sensor 80*c* positioned along a flow line 138 from blower 20 (e.g., such line directly output from blower 20 or branching off of the main flow line directed toward inspiration flow outlet 130). The flow line 138 may lead to an exhalation valve interface 134 for connecting an exhalation valve control line 98 used for controlling exhalation valve 96.

Ventilation system 12*a* may also include a proximal pressure sensor 80*b* connected to a proximal pressure interface 136 configured for connecting a proximal pressure line 100, which may run along limb 90 or 92 of breathing circuit 16. Proximal pressure sensor 80*b* may monitor the gas pressure delivered toward the patient when proximal pressure line 100 is connected to ventilation system 12.

Any of the various sensors and/or valves of system 12*a* may communicate signals to gas delivery control system 31, which may process such signals and control the speed of turbine 20 accordingly. Gas delivery control system 31 may also communicate control signals to control the operation of any of the valves of system 12*a*.

FIG. 6 illustrates an example arrangement of various components of example ventilation system 12*a*, according to one embodiment of the present disclosure. Beginning at the air intake pathway, ventilation system 12*a* may include air inlet filter 140 leading to first silencer 150 of a turbine-based blower module. Intake air may then be compressed by turbine 20 and delivered through second silencer 152 and along the main flow line 190 toward the connection interface 130 for the inhalation limb of a breathing circuit 16.

A check valve 160 may be located along main flow line 190. Check valve 160 may comprise a mechanical (e.g., spring-based) or pneumatic relief valve configured to automatically open in the event of an overpressure situation. Some embodiment may not include check valve 160. Inhalation flow sensor 82*a* and inhalation pressure sensor 80*a* may also be located along main flow line 190, and configured to measure the flow rate and pressure in main flow line 190.

An $O_2$ inlet 154 may be configured for connecting a supplemental oxygen source. An $O_2$ safety valve 156 may be located along $O_2$ flow line 192, and configured to slow or stop the flow of supplemental oxygen in certain situations, e.g., as discussed above regarding FIGS. 4A and 4B. $O_2$ flow line 192 may lead to a mixing chamber or area such that the supplemental oxygen may mix with the output air from turbine 20 and continue toward patient 11 along main flow line 190 inhalation limb connection interface 130 as an air-$O_2$ mixture.

An exhalation limb connection interface 132 provides an interface for connecting an exhalation limb of a breathing circuit 16, and leads to an exhalation flow line 194. An exhalation flow sensor 82*b* for measuring the exhalation flow rate is located along exhalation flow line 194 before the flow is directed out of and away from system 12.

An exhalation valve control line interface 134 provides an interface for connecting an exhalation valve control line for controlling an exhalation valve in a breathing circuit 16. Exhalation valve control line interface 134 is connected to the turbine-based blower module via a pressurized control line 196 such that pressurized gas can be applied to the exhalation valve in order to control the exhalation valve. A pilot valve 102 (e.g., a solenoid) may control the pressure within control line 196. Pilot valve 102 may be controlled by signals from CPU 22, which may be generated based on pressure measurements from a pressure sensor 80*c* located along control line 196.

A user interface module 40 may include a display (e.g., an LCD or other screen) and a keypad 42 including any number and/or type of keys, buttons, switches, or other manual interfaces. CPU 22 may include any one or more processor configured to communicated with and/or control any of the various components of system 12*a*. CPU 22 may include or may have access to any software, firmware, algorithms, or other logic or instructions for performing any of the various control functions discussed herein.

Various components may be physically located on a circuit board. In this example, CPU, sensors 80*a*, 80*c*, 80*c*, 82*a*, and 82*b*, and user interface module 40 are located on a circuit board 198.

CPU 22 may control a turbine control device 200 configured to control the operation of turbine 20. Turbine control device 200 may be configured to provide any suitable performance characteristics, as desired. For instance, in an example embodiment, turbine control device 200 is designed according to the following performance characteristics:

The device drives from 0 to 45,000 rpm a 3-phase brushless motor with position or motor speed sensors;

The device transfers signals from a motor position or motor speed sensor;

The device transfers signals from a motor temperature sensor;

The device allows the motor supply to be cut by an external control;

The device allows breaking of the motor by an external source;

The inrush current of the device is less than 3A; and

The power supply current is less than 3A.

CPU 22 may control turbine control device 200 based on any suitable data, e.g., data from one or more sensors and/or data input by a user via user interface module 40.

One or more data ports 206 may provide a connection interface for communicating data to and/or from system 12 (e.g., CPU 22). Each data port 206 may comprise any suitable type of data port, e.g., a USB, Ethernet, FireWire, or RS-232 port.

A repeater interface 202 provides an interface for connecting a wireless notification module 44 for wirelessly communicating data (e.g., alarms and/or other data) to wireless receiving devices via one or more wireless repeaters. Such system is discussed below with reference to FIG. 7.

An FiO2 socket 204 for connecting a FiO2 sensor (e.g., oxygen cell) for providing measurements of the oxygen concentration (or percent oxygen) of the gas delivered toward patient 11. Ventilation system 12 may use such measurements for monitoring the oxygen concentration in the patient air flow, e.g., for triggering Low and High FiO2 alarms based on Low and High FiO2 thresholds (which may be set by a user via GUI 40, automatically determined by system 12, or otherwise determined).

A power system 30 may include a battery 50, an AC/DC power supply and battery charger 124, and a power switchover 126, e.g., as discussed above with reference to FIG. 3. An AC/DC source interface 210 and an on/off switch 212 may be connected to AC/DC power supply and battery charger 124.

Wireless Notification System

Figure 7:
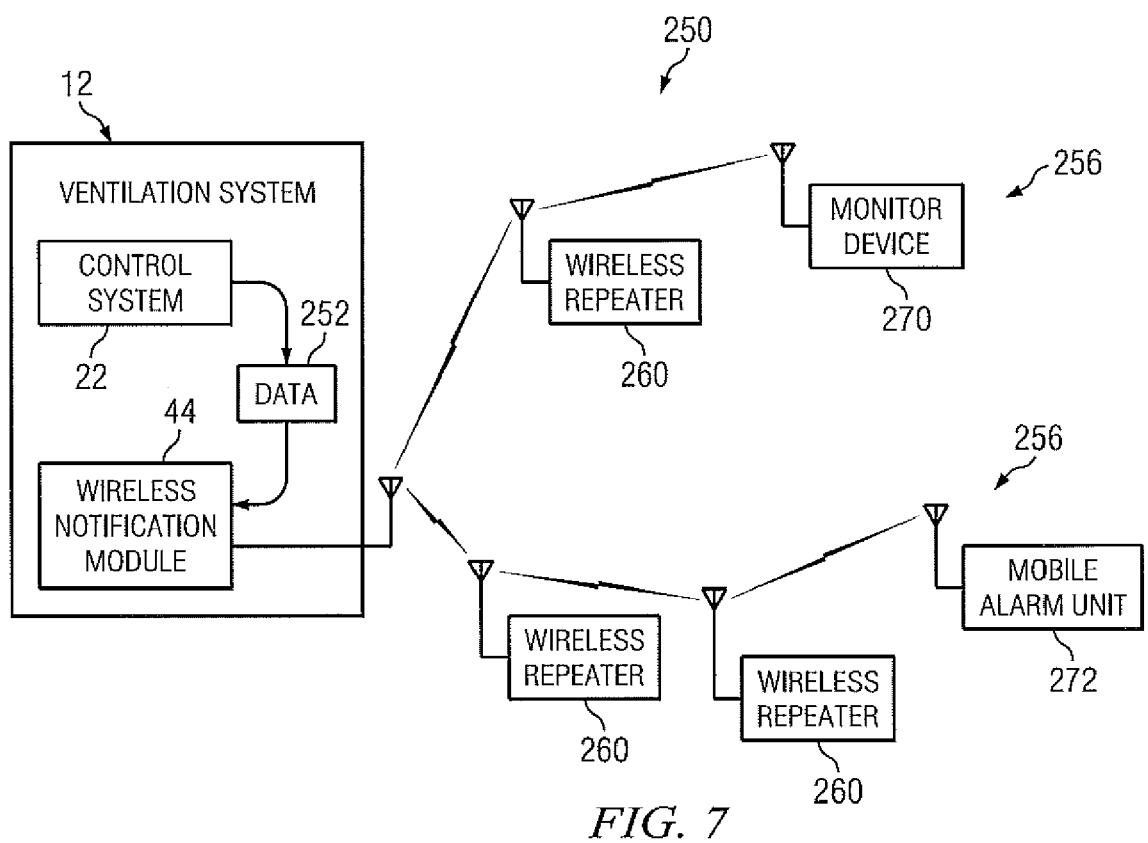
FIG. 7 illustrates an example wireless notification system configured to communicate wireless notifications (e.g., alarms) from a ventilation system to one or more receiving devices, according to certain embodiments of the present disclosure.

FIG. 7 illustrates an example wireless notification system 250 configured to communicate wireless notifications (e.g., alarms generated by control system 22) from ventilation system 12 to one or more receiving device, e.g., a remote monitor or a mobile alarm unit carried by a user (e.g., a caretaker). In some embodiments, wireless notification system 250 may include a wireless notification module 44 included in or coupled to ventilation system 12, one or more wireless repeaters 260, and one or more wireless receiving devices 256. In general, wireless notification module 44 may be configured to wirelessly transmit alarms or other data to wireless receiving devices 256, either directly or via one or more wireless repeaters 260.

Wireless notification module 44 may be included in or coupled to ventilation system 12. For example, module 44 may be integrated with ventilation system 12. Alternatively, module 44 may be a separate module that may be connected to an interface of ventilation system 12 via any suitable wireline or wireless interface, e.g., USB, Ethernet, or Bluetooth connection. In the example embodiment shown in FIG. 6, module 44 may be configured to connection to ventilation system 12 via repeater interface 202. Wireless notification module 44 may include any hardware, software, firmware, etc. for communicating with components of ventilation system 12 (e.g., control system 22) and wirelessly communicating data 252 from such components of ventilation system 12 to one or more wireless receiving devices 256, either directly or via one or more wireless repeaters 260. In an example embodiment, wireless notification module 44 may include an RF modem configured to transmit and/or receive wireless signals.

Each wireless repeater 260 may comprise any type of known repeater for wirelessly relaying data 252 between two devices (e.g., between a computing device and a wireless access point). More particularly, each wireless repeaters 260 may relay data (a) between wireless notification module 44 and a receiving device 256, (b) between wireless notification module 44 and another wireless repeater 260, and (c) between two other wireless repeaters 260. In this manner, wireless repeaters 260 facilitate communication of data 252 between wireless notification module 44 and receiving devices 256.

Wireless notification system 250 may include any number of wireless repeater 260 positioned and at any suitable locations. For example, wireless repeaters 260 may be aligned in a row to provide wireless coverage for a distance in one direction, or may be arranged in an array to provide wireless coverage over a desired area. In some embodiments, wireless repeaters 260 may be located in multiple rooms throughout a building to provide wireless coverage throughout the building.

Wireless receiving devices 256 may include any one or more types of devices configured to (a) wirelessly receive data 252 from wireless notification module 44, either directly or via one or more wireless repeaters 260 and (b) communicate the received data 252 to a person (e.g., a caretaker) remote from ventilation system 12. A wireless receiving devices 256 may communicate data 252 to a person in any suitable manner, e.g., (a) visually displaying the data via a visible display device (e.g., a screen, monitor, LEDs, etc.), (b) generating various audible sounds or voice messages via a speaker or other suitable device, (c) vibrating, or (d) any combination of the above.

Wireless receiving devices 256 may include one or more monitor devices 270 and mobile alarm units 272. A monitor device 270 may comprise any device having a monitor or screen for visually displaying data 252. For example, monitor device 270 may comprise a monitor or screen of a computer, a television, or a stand-alone monitor device. Mobile alarm units 272 may include any mobile device that may be carried by a person, e.g., a hand-held device or a device that may be attached to the person's clothing. Mobile alarm units 272 may include devices having other functionality not related to wireless notification system 250 (e.g., a mobile phone, PDA, or portable computer) and/or devices specifically designed for wireless notification system 250. For certain device (e.g., mobile phone, PDA, or portable computers having other, unrelated functionality), software may be installed onto such devices in order to provide the relevant functionality (e.g., data communication, processing, and display functionality) of a wireless receiving devices 256 for use in wireless notification system 250.

Data 252 may include any type of data regarding the condition of patient 11 and/or the operation of breathing assistance system 10. In some embodiments, data 252 includes alarm data, e.g., notifications of alarms generated by any of the sub-systems of control system 22 (including, for example, any of the various alarms discussed herein). Some alarms may indicate any fault or malfunction regarding the operation of any one or more sub-system or component of breathing assistance system 10. Other alarms may indicate a dangerous or potentially dangerous physiological condition of patient 11.

In other embodiments, data 252 includes alarm data as well as other data regarding patient 11 and/or breathing assistance system 10, e.g., ventilator settings, sensor readings (e.g., pressure, flow, and temperature data), and/or physiological measurements regarding patient 11. In some embodiments, data 252 (e.g., ventilator settings, sensor readings, and/or physiological measurements) may be continuously or substantially continuously communicated to wireless receiving devices 256 such that the data may be continuously or substantially continuously displayed and updated by the wireless receiving devices 256.

Data 252 may also include data identifying the particular ventilation system 12 and/or the particular patient 11. In some configurations, data 252 may include "heartbeat" signals or other signals for indicating the presence and/or operational status of the communicating device.

As discussed above, in some embodiments or configurations, wireless notification module 44 may communicate data 252 to wireless receiving devices 256 continuously or substantially continuously. Such communications may include alarms and/or other data.

In other embodiments or configurations, wireless notification system 250 is essentially a remote alarm system, designed mainly for communicating alarms. In some such embodiments, wireless notification module 44 may maintain continuous (or frequent) communications with wireless receiving devices 256, e.g., my "heartbeat" signals or other signals indicating the presence and/or operational status (e.g., "powered on") of each wireless receiving device 256. When an alarm condition occurs in system 10, wireless notification module 44 may interrupt the continuous (or frequent) communications with wireless receiving devices 256; in response to the interrupt in communications, each wireless receiving device 256 may generate an alarm. Each wireless receiving device 256 may also generate an alarm if it moves outside the range for receiving communications from wireless notification module 44 (e.g., if device 256 cannot communicate with wireless notification module 44 or any wireless repeater 260).

Alternatively, when an alarm condition occurs in breathing assistance system 10, wireless notification module 44 may transmit an alarm signal (as data 252) to wireless receiving devices 256 (again, either directly or via one or more repeaters 260), and in response, each wireless receiving device 256 may generate an alarm (e.g., an audible or visible alarm). In some embodiments, wireless receiving device 256 may generate a first type of alarm when it receives an alarm signal transmitted by wireless notification module 44, and a second first type of alarm when communications with wireless notification module 44 are interrupted (e.g., due to moving outside the range of communication with wireless notification module 44 or any wireless repeater 260, or due to a fault associated with any component of wireless notification module 44.

Components of wireless notification system 250 (e.g., wireless notification module 44, wireless repeaters 260, and wireless receiving devices 256) may be powered in any suitable manner, e.g., by battery or from an electrical power grid (e.g., via an A/C wall outlet). For example, in some embodiments, wireless notification module 44 may be powered by power system 30 of ventilation system 12, wireless repeaters 260 may plugged into a wall outlet or powered by battery, and wireless receiving devices 256 may be powered by rechargeable battery. In some embodiments, components of wireless notification system 250 operating on battery power may generate a low battery alarm when appropriate. Such alarm may notify the user to replace or recharge the battery.

In some embodiments, wireless notification system 250 may utilize power management techniques for reducing power used by various system components (e.g., wireless notification module 44, wireless repeaters 260, and wireless receiving devices 256). For example, various system components may enter a low power mode (e.g., a sleep, standby, or low power mode) when not communicating data, in order to conserve power. System components may be awakened or enter a full power or powered up mode as appropriate in order to transmit and/or receive data. For example, one system component (e.g., wireless notification module 44) may communicate a "wakeup" signal to wireless repeaters 260 and/or wireless receiving devices 256 in order to awaken such components for receiving and/or transmitting data. Such "wakeup" signals may be communicated periodically or at any other time for communicating data 252. Alternatively, various system components may be synchronized and awaken themselves in a synchronized manner in order to communicate data 252. In such embodiments, each system component may maintain a clock, and synchronization signals may be communicated among the system components periodically in order to keep the component clocks synchronized.

Any of the components of wireless notification system 250 (e.g., wireless notification module 44, wireless repeaters 260, and wireless receiving devices 256) may include any hardware, software, and/or firmware for transmitting and/or receiving wireless communications of data (e.g., data 252). For example, components of wireless notification system 250 may include any suitable wireless transmitters, wireless receivers, and/or wireless transceivers. In some embodiments, each of wireless notification module 44, wireless repeaters 260, and wireless receiving devices 256 include both transmitters and receivers (or transceivers) such that data may be communication in both directions between wireless notification module 44 and wireless receiving devices 256.

The wireless communications between the various components of wireless notification system 250 may use any known protocol or standard. Examples of wireless communication protocols that may be used include, but are not limited to, personal area networks (PAN) (e.g., BLUETOOTH), local area networks (LAN), wide area networks (WAN), narrowband personal communications services (PCS), broadband PCS, circuit switched cellular, cellular digital packet data (CDPD), radio frequencies, such as the 800 MHz, 900 MHz, 1.9 GHz and 2.4 GHz bands, infra-red and laser.

In some embodiments, wireless notification system 250 may fixed-frequency communications. In other embodiments, wireless notification system 250 may spread-spectrum communications, e.g., by means of frequency-hopping, direct sequence, or any other known techniques.

In some embodiments, wireless receiving devices 256 may communicate data to wireless notification module 44. For example, each wireless receiving device 256 may communicate identification data and/or location data to wireless notification module 44 at any suitable time, for example, substantially continuously, periodically, or in response to some triggering event (e.g., wireless receiving device 256 being turned on or preparing to communicate a control signal to wireless notification module 44, for example, to remotely change a ventilation setting).

In some embodiments, wireless notification system 250 may include an identification or security system to ensure that only authorized devices are communicating in system 250. Some or all system components may store identification data that may be communicated to other system components for authentication of system components. For example, in order to enter a communication session with wireless notification module 44, the wireless receiving device 256 may communicate identification data to module 44 at any suitable time, for example, periodically, upon powering up device 256, module 44, or ventilation system 12, or in response to a request by module 44. Thus, wireless notification module 44 may manage the authentication process. In other embodiments, wireless repeaters 260 may be configured to manage the authentication process.

Example Methods of Operation

Figure 8:
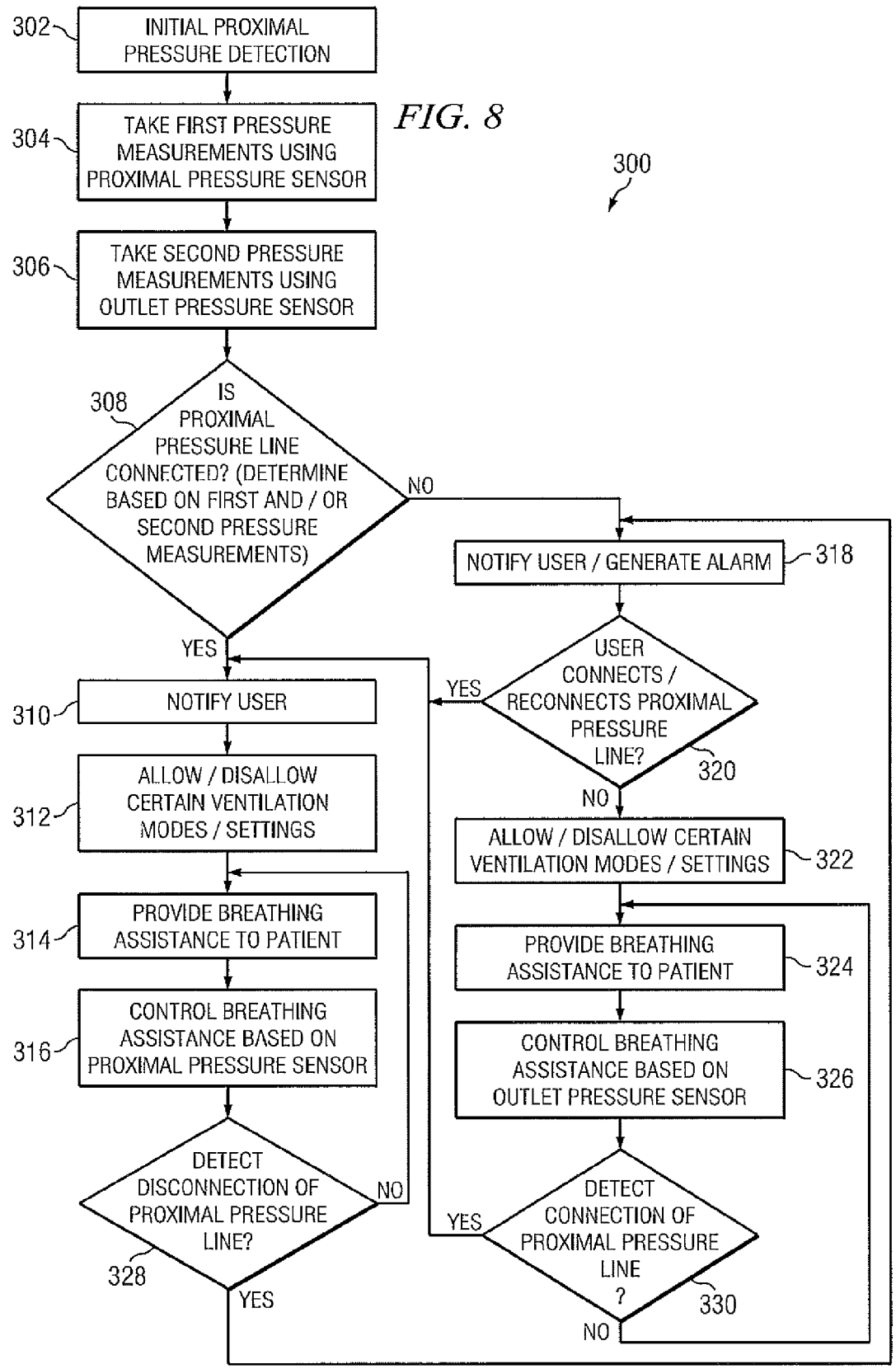
FIG. 8 illustrates an example method of using multiple pressure sensors for managing control of a ventilation system, according to certain embodiments of the present disclosure.

FIG. 8 illustrates an example method 300 of using multiple pressure sensors for managing control of a ventilation system 12, according to certain embodiments of the present disclosure. The example method 300 uses two pressure sensors for managing control of ventilation system 12. In particular, in the discussion below, the two pressure sensors are outlet pressure sensor 80a and proximal pressure sensor 80b. However, method 300 may similarly apply to other pairs of pressure sensors provided in breathing assistance system 10, depending on the specific embodiment. Such pair of pressure sensors may be positioned at any location in breathing assistance system 10, and may be configured to measure pressure at any different locations within breathing assistance system 10, e.g., any locations along a conduit of ventilation system 12 and/or connection system 14. In addition, although example method 300 uses two pressure sensors for managing control of ventilation system 12, similar techniques may be used for managing control of ventilation system 12 using more than two (e.g., 3 or more) pressure sensors.

At step 302, a proximal pressure detection process is initiated. Such process may be initiated automatically upon a triggering event (e.g., turning on ventilation system 12, user or automatic selection of a particular ventilation mode or setting, or execution of a start-up test) or based on a user-initiated request. In general, as discussed below, the proximal pressure detection process determines whether a proximal pressure line 100 is connected to ventilation system 12 such that proximal pressure sensor 80b may effectively measure the proximal pressure (e.g., pressure in connection system 14 near patient 11) for use in controlling the operation of ventilation system 12 (e.g., whether proximal pressure sensor 80b may be used by gas delivery control system 31 may control the pressure and/or flow of gas delivered toward patient 11).

At step 304, proximal pressure sensor 80b may take and communicate one or more pressure measurements to proximal pressure detection system 36. Proximal pressure sensor 80b may communicate a single pressure measurement or multiple pressure measurements over any suitable time period.

At step 306, outlet pressure sensor 80a may take and communicate one or more pressure measurements to proximal pressure detection system 36. Outlet pressure sensor 80a may communicate a single pressure measurement or multiple pressure measurements over any suitable time period. Steps 304 and 306 may be performed in any order and/or substantially simultaneously.

At step 308, proximal pressure detection system 36 may determine whether a proximal pressure line 100 is connected to ventilation system 12 such that proximal pressure sensor 80b may effectively measure the proximal pressure (e.g., the pressure in connection system 14 near patient 11). Proximal pressure detection system 36 may determine whether a proximal pressure line 100 is connected based at least on (a) pressure measurements from proximal pressure sensor 80b at step 304, (b) pressure measurements from outlet pressure sensor 80a at step 306, or (c) both.

For example, proximal pressure detection system 36 may compare measurement(s) from proximal pressure sensor 80b with measurement(s) from outlet pressure sensor 80a, and determine that a proximal pressure line 100 is connected if the proximal pressure sensor 80b measurement(s) is/are greater than the outlet pressure sensor 80a measurement(s), and that a proximal pressure line 100 is not connected if the proximal pressure sensor 80b measurement(s) is/are less than or equal to than the outlet pressure sensor 80a measurement(s).

As another example, proximal pressure detection system 36 may determine that a proximal pressure line 100 is connected if the proximal pressure sensor 80b measurement(s) is/are greater than the outlet pressure sensor 80a measurement(s), but by an amount within a threshold pressure difference (e.g., determined based on empirical data). In such embodiments, such threshold pressure difference may be selected from a set or range of predetermined threshold pressure difference based on the particular flow rate at which the outlet pressure sensor 80a measurement(s) were taken. Such set or range of predetermined threshold pressure difference may be used to account for the fact that, in certain configurations, the expected difference in pressure measurements between outlet pressure sensor 80a and proximal pressure sensor 80b (e.g., due to pressure drop within connection system 14) depends on the flow rate through connection system 14. Thus, the higher the flow rate through connection system 14 during the pressure measurements at steps 304 and/or 306, the higher the expected difference between proximal pressure sensor 80b measurement(s) and outlet pressure sensor 80a measurement(s), and thus the higher the threshold pressure difference that should be used.

Note that these two examples assume positive direction flow (i.e., toward patient 11); for negative direction flow (i.e., away from patient 11), the analysis would be reversed.

As another example, proximal pressure detection system 36 may compare the proximal pressure sensor 80b measurement(s) to a threshold pressure value (e.g., determined based on empirical data), and determine that a proximal pressure line 100 is connected if the proximal pressure sensor 80b measurement(s) is/are greater than the threshold pressure value, and that a proximal pressure line 100 is not connected if the proximal pressure sensor 80b measurement(s) is/are less than or equal to the threshold pressure value.

As another example, proximal pressure detection system 36 may compare the proximal pressure sensor 80b measurement(s) to a predetermined expected pressure value (e.g., determined based on empirical data), and determine that a proximal pressure line 100 is connected if the proximal pressure sensor 80b measurement(s) do not differ from the predetermined expected pressure value by more than a predetermined threshold value.

In other embodiments, proximal pressure detection system 36 may analyze (a) proximal pressure sensor 80b measurement(s), (b) outlet pressure sensor 80a measurement(s), or (c) both, in any other manner to determine whether a proximal pressure line 100 is connected to ventilation system 12.

If proximal pressure detection system 36 determines at step 308 that a proximal pressure line 100 is connected to ventilation system 12, the method may advance to step 310. At step 310, system 36 may generate and/or display to the user a notification that a proximal pressure line 100 is connected and/or that proximal pressure sensor 80b measurement(s) will or may be used for controlling aspects of ventilation system 12.

At step 312, control system 31 may allow or disallow particular ventilation modes or settings based on the determination that a proximal pressure line 100 is connected to ventilation system 12 (and that proximal pressure sensor 80b measurement(s) may be used for controlling ventilation system 12). For example, control system 31 may allow user or automatic selection of, and/or automatic switching to, certain ventilation modes or settings that require accurate patient pressure readings that may be provided by proximal pressure sensor 80b but not by outlet pressure sensor 80a. As discussed below at step 322, one or more of such ventilation modes or settings may be disallowed if it is determined that a proximal pressure line 100 is not connected to ventilation system 12.

At step 314, ventilation system 12 may provide breathing assistance to patient 11 according to ventilation settings (e.g., a ventilation mode and/or parameter settings) selected manually by a user and/or automatically by control system 31. One or more of such ventilation settings may be determined by the determination at step 312.

At step 316, control system 22 may control operational aspects of ventilation system 12 based at least on proximal pressure measurements from proximal pressure sensor 80b. For example, gas delivery control system 31 may control the pressure and/or flow rate of gas delivered toward patient 11 based on proximal pressure measurements from sensor 80b. As another example, if an exhalation valve 96 is connected to system 12, control system 22 may control exhalation valve 96 (e.g., by controlling pilot valve 102) based on proximal pressure measurements from sensor 80b.

Alternatively, if proximal pressure detection system 36 determines at step 308 that a proximal pressure line 100 is not connected to ventilation system 12, the method may advance to step 318. At step 318, system 36 may generate and/or display to the user a notification or alarm that a proximal pressure line 100 is not connected and/or that proximal pressure sensor 80b measurement(s) will not be used (or that for outlet pressure sensor 80a measurement(s) will be used) for controlling aspects of ventilation system 12.

At step 320, proximal pressure detection system 36 may allow the user to respond to the alarm displayed at step 318 before beginning or continuing breathing assistance to patient 11. For example, system 36 may display a user-selectable option to connect a proximal pressure line 100 or to continue without a proximal pressure line 100. If the user connects a proximal pressure line 100, the method may advance to step 312. If the user selects to continue without a proximal pressure line 100, the method may advance to step 322. In some embodiments, step 320 may be excluded, wherein the method may automatically advance from step 318 to step 322.

At step 322, control system 31 may allow or disallow particular ventilation modes or settings based on the determination that a proximal pressure line 100 is not connected to ventilation system 12 (and that proximal pressure sensor 80b measurement(s) may not be used for controlling ventilation system 12). For example, control system 31 may disallow user or automatic selection of, and/or automatic switching to, certain ventilation modes or settings that require accurate patient pressure readings that may be provided by proximal pressure sensor 80b but not by outlet pressure sensor 80a.

At step 324, ventilation system 12 may provide breathing assistance to patient 11 according to ventilation settings (e.g., a ventilation mode and/or parameter settings) selected manually by a user and/or automatically by control system 31. One or more of such ventilation settings may be determined by the determination at step 322.

At step 326, control system 22 may control operational aspects of ventilation system 12 based at least on outlet pressure measurements from outlet pressure sensor 80a. For example, gas delivery control system 31 may control the pressure and/or flow rate of gas delivered toward patient 11 based on outlet pressure measurements from sensor 80a. As another example, if an exhalation valve 96 is connected to system 12, control system 22 may control exhalation valve 96 (e.g., by controlling pilot valve 102) based on outlet pressure measurements from sensor 80a. In some embodiments, outlet pressure measurements from sensor 80a may be "corrected" (e.g., to compensate for pressure drop within connection system 14) using any suitable technique, e.g., any of the techniques disclosed in pending EP Patent Application EP 08006240.9, filed on Mar. 31, 2008, and entitled "Systems and Methods for Compensating for Pressure Drop in a Breathing Assistance System."

While providing breathing assistance to patient 11, proximal pressure detection system 36 may continue to determine whether a proximal pressure line 100 is connected to system 12 periodically, continuously, in response to a detected event or user request, or at any other time. In this manner, control system 22 may adjust to a connection or disconnection of a proximal pressure line 100 while system 12 is providing breathing assistance to patient 11. Such detection may include, for example, the techniques discussed above at steps 304-308.

As shown at step 328, if ventilation system 12 is providing breathing assistance using proximal pressure sensor 80b measurements for controlling various operational aspects, and system 36 detects disconnection of proximal pressure line 100, the method may advance to steps 318-326 to switch from proximal pressure sensor 80b measurement to outlet pressure sensor 80a measurements. Thus, for example, system 36 may generate a user alarm indicating disconnection of proximal pressure line 100 (at step 318), allow the user to re-connect proximal pressure line 100 or continue without proximal pressure line 100 (at step 320), allow or disallow particular ventilation modes or settings based on the determination that proximal pressure line 100 is not connected (at step 322), provide breathing assistance according to the now relevant ventilation settings (at step 324), and control operational aspects of ventilation system 12 based on outlet pressure sensor 80a measurements (at step 326).

Similarly, as shown at step 330, if ventilation system 12 is providing breathing assistance using outlet pressure sensor 80a measurements for controlling various operational aspects, and system 36 detects connection (or reconnection) of a proximal pressure line 100, the method may advance to steps 310-316 to switch from outlet pressure sensor 80a measurements to proximal pressure sensor 80b measurements. Thus, for example, system 36 may generate a user notification indicating connection of proximal pressure line 100 (at step 310), allow or disallow particular ventilation modes or settings based on the determination that proximal pressure line 100 is connected (at step 312), provide breathing assistance according to the now relevant ventilation settings (at step 314), and control operational aspects of ventilation system 12 based on proximal pressure sensor 80a measurements (at step 316).

Figure 9:
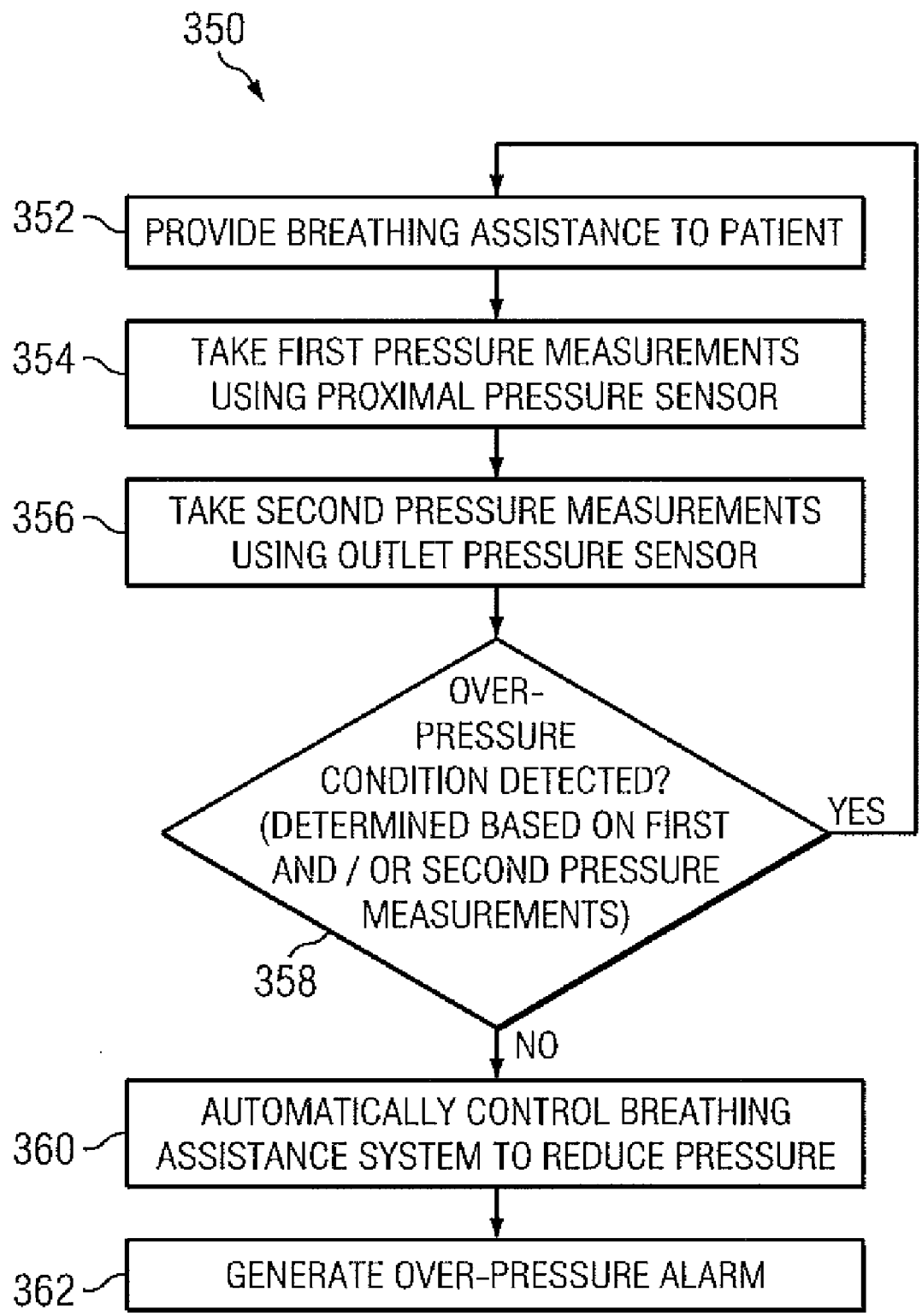
FIG. 9 illustrates an example method for detecting and managing an over-pressure condition in a breathing assistance system, according to certain embodiments of the present disclosure.

FIG. 9 illustrates an example method 350 for detecting and managing an over-pressure condition in a breathing assistance system 10, according to certain embodiments of the present disclosure. For example, method 350 may be used for detecting an over-pressure condition in connection system 14 (e.g., in breathing circuit 16) based on pressure signals received from one or more pressure sensors 24 and managing a detected over-pressure condition.

The example method 350 uses two pressure sensors, either separately or in combination, for detecting an over-pressure condition in breathing assistance system 10. In particular, in the discussion below, the two pressure sensors are outlet pressure sensor 80a and proximal pressure sensor 80b. However, method 350 may similarly apply to other pairs of pressure sensors provided in breathing assistance system 10, depending on the specific embodiment. Such pair of pressure sensors may be positioned at any location in breathing assistance system 10, and may be configured to measure pressure at any different locations within breathing assistance system 10, e.g., any locations along a conduit of ventilation system 12 and/or connection system 14. In addition, although example method 350 uses two pressure sensors for detecting an over-pressure condition in breathing assistance system 10, similar techniques may be used for detecting an over-pressure condition using more than two (e.g., 3 or more) pressure sensors, either separately or in combination.

At step 352, ventilation system 12 may provide breathing assistance to patient 11, e.g., according to ventilation settings (e.g., a ventilation mode and/or parameter settings) selected manually by a user and/or automatically by control system 31.

At step 354, proximal pressure sensor 80b may take and communicate one or more pressure measurements to proximal pressure detection system 36. Proximal pressure sensor 80b may communicate a single pressure measurement or multiple pressure measurements over any suitable time period. In some embodiments or configurations, proximal pressure sensor 80b may be configured to measure a proximal pressure near patient 11 via a proximal pressure line 100 connected at one end to ventilation system 12 and extending along a limb of breathing circuit 16.

At step 356, outlet pressure sensor 80a may take and communicate one or more pressure measurements to proximal pressure detection system 36. Outlet pressure sensor 80a may communicate a single pressure measurement or multiple pressure measurements over any suitable time period. In some embodiments or configurations, outlet pressure sensor 80a may be located at or near a main gas outlet of ventilation system 12 (e.g., at or near an outlet of gas delivery system 20) to measure the pressure of gas flow exiting ventilation system 12 or gas delivery system 20, or the pressure of gas flow entering connection system 14. The two sensors 80a and 80b may detect different pressure levels, e.g., due to pressure drop inherent in breathing circuit 16.

Steps 354 and 356 may be performed in any order and/or substantially simultaneously.

At step 358, over-pressure security system 32 may determine whether an over-pressure condition is present in system 10 (e.g., in connection system 14). For example, over-pressure security system 32 may compare pressure measurements received from sensors 80a and 80b to one or more threshold pressure values to automatically detect an over-pressure condition. Pressure measurements from both sensors 80a and 80b may each be compared to a single pressure threshold value, or each sensor's measurements may be compared to a separate corresponding pressure threshold value. Such pressure threshold value(s) may be determined in any suitable manner, and may be manually or automatically adjusted over time.

In some embodiments, over-pressure security system 32 may compare pressure measurements received from sensors 80a and 80b to different pressure threshold values to account for differences between expected pressure measurements from sensors 80a and 80b, e.g., due to pressure drop in connection system 14. The pressure threshold values for comparing pressures from each of sensors 80a and 80b may be determined in any suitable manner (e.g., stored values based on empirical data).

In some embodiments, one or both of threshold pressure values may be selected (e.g., using an algorithm or look-up table) based on the particular flow rate at which such measurements by sensors 80a and/or 80b were taken. Thus, one or both of threshold pressure values may be selected from a range of values to account for the fact that, in certain configurations, the expected difference in pressure measurements from sensor 80a and sensor 80b (e.g., due to pressure drop within connection system 14) depends on the flow rate through connection system 14.

In some embodiments, over-pressure security system 32 may determine that an over-pressure condition is present if either (a) the pressure measured by proximal pressure sensor 80a exceeds its corresponding threshold value or (b) the pressure measured by proximal pressure sensor 80a exceeds its corresponding threshold value (which may be the same as, or different from, the corresponding threshold value for proximal pressure sensor 80a measurements, as discussed above). In such embodiments, using both sensors 80a and 80b may provide a level of redundancy for protecting against over-pressure situations.

In other embodiments, over-pressure security system 32 may determine that an over-pressure condition is present only if both (a) the pressure measured by proximal pressure sensor 80a exceeds its corresponding threshold value and (b) the pressure measured by proximal pressure sensor 80a exceeds its corresponding threshold value (which may be the same as, or different from, the corresponding threshold value for proximal pressure sensor 80a measurements, as discussed above).

If over-pressure security system 32 does not determine an over-pressure condition at step 358, the method may return to steps 352-358 to continue providing breathing assistance, take pressure measurements, and determine whether an over-pressure condition arises. Steps 354-358 may be repeated at any time interval, e.g., substantially continuously, periodically, or in response to some triggering event.

Alternatively, if over-pressure security system 32 determines an over-pressure condition at step 358, system 32 may manage the over-pressure condition at step 360. For example, over-pressure security system 32 may notify gas delivery control system 31 such that system 31 controls gas delivery system 20 to end the over-pressure condition, e.g., by (a) reducing the pressure or flow rate produced by gas delivery system 20 (e.g., to a pressure at or just below a threshold pressure value, or to a lower pressure) or (b) shutting down gas delivery system 20. For example, in embodiments in which gas delivery system 20 includes a blower (e.g., a turbine-based blower), gas delivery control system 31 may reduce the speed of the blower.

At step 362, over-pressure security system 32 may generate an over-pressure alarm. The alarm may comprise any notification that may be sensed by a user, e.g., an audible alarm or a visible alarm displayed to the user, e.g., via display 28 or separate device (e.g., an LED).

In some configurations, monitoring signals from both sensors 80a and 80b as discussed above may provide redundancy to account for situations in which 80a or 80b is not providing useful data, e.g., where one of sensors 80a and 80b is damaged or not working properly, or where a proximal pressure line 100 is not used or is blocked.

Figure 10:
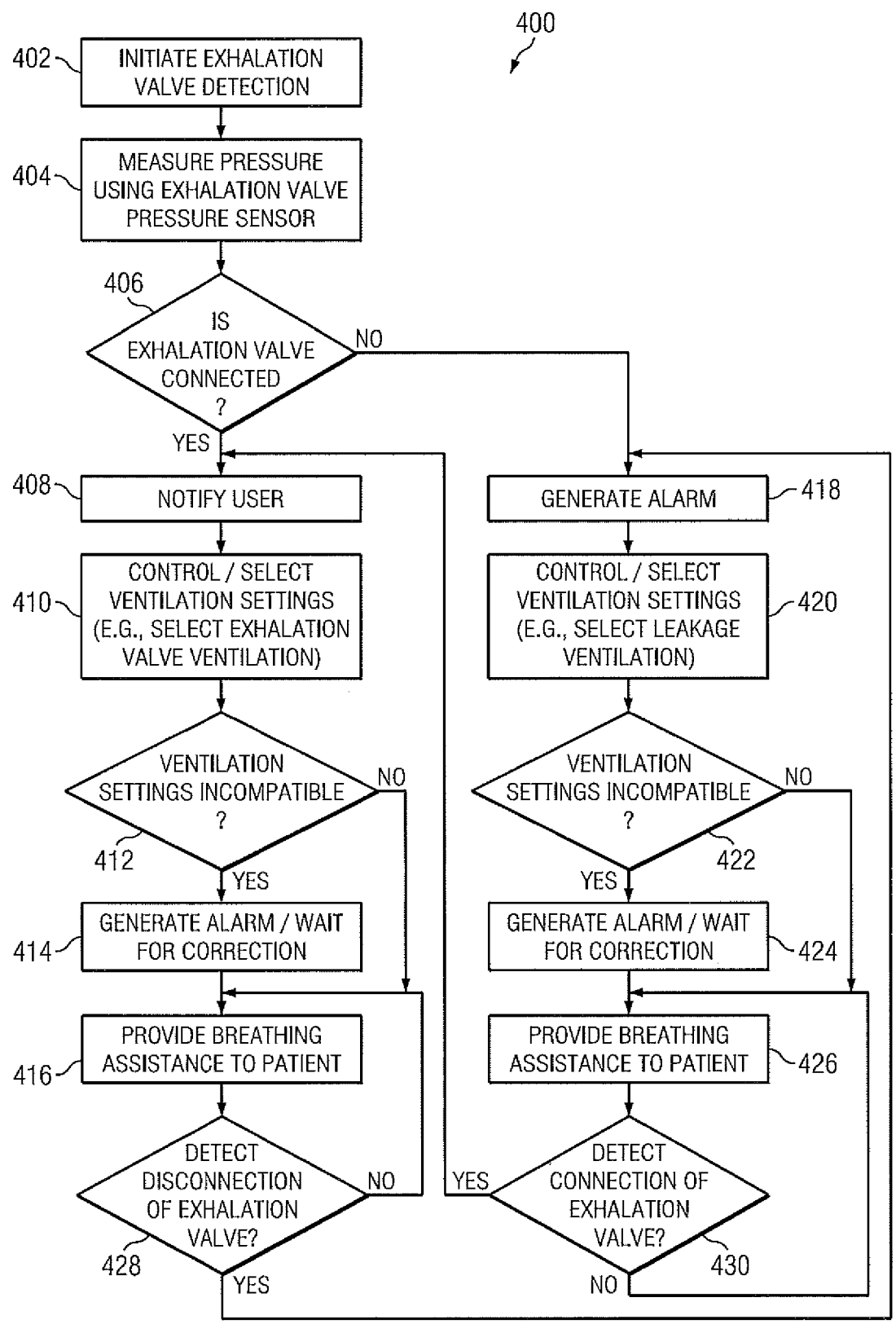
FIG. 10 illustrates an example method for determining whether an exhalation valve is connected to a ventilation system, and controlling the ventilation system accordingly, according to certain embodiments of the present disclosure.

FIG. 10 illustrates an example method 400 for determining whether an exhalation valve 96 is connected to ventilation system 12, and controlling ventilation system 12 accordingly, according to certain embodiments of the present disclosure.

At step 402, an exhalation valve detection process is initiated. Such process may be initiated automatically upon a triggering event (e.g., turning on ventilation system 12, user or automatic selection of a particular ventilation mode or setting, or execution of a start-up test) or based on a user-initiated request. In general, as discussed below, the exhalation valve detection process determines whether an exhalation valve 96 is connected to ventilation system 12 (e.g., via an exhalation valve control line 98) such that ventilation system 12 may control exhalation valve 96 while providing breathing assistance to patient 11.

At step 404, exhalation valve sensor 80c may take and communicate one or more pressure measurements to exhalation valve detection system 34. Exhalation valve sensor 80c may communicate a single pressure measurement or multiple pressure measurements over any suitable time period.

At step 406, exhalation valve detection system 34 may determine whether an exhalation valve 96 is connected to ventilation system 12 (e.g., via an exhalation valve control line 98) based at least on pressure measurements from exhalation valve sensor 80c. For example, exhalation valve detection system 34 may compare measurement(s) from exhalation valve sensor 80c to a threshold pressure value to automatically determine whether an exhalation valve 96 is connected. Generally, if no exhalation valve 96 is connected, the connection port for exhalation valve control line 98 may remain open, and thus the pressure measured by exhalation valve sensor 80c may remain low (e.g., below the threshold pressure value). However, if an exhalation valve 96 is connected via an exhalation valve control line 98 connected to ventilation system 12, the pressure measured by exhalation valve sensor 80c may increase (e.g., above the threshold pressure value). The threshold pressure value may be determined in any suitable manner (e.g., stored value(s) based on empirical data), and may be manually or automatically adjusted over time.

If exhalation valve detection system 34 determines that an exhalation valve 96 is connected to ventilation system 12, the method may proceed to step 408. Otherwise, the method may proceed to step 418.

At step 408, exhalation valve detection system 34 may generate and display a user notification that an exhalation valve 96 is connected and/or being used for controlling breathing assistance.

At step 410, gas delivery control system 31 may automatically select between different ventilation modes or settings or otherwise control one or more ventilation parameters (e.g., flow and/or pressure) based on the determination that an exhalation valve 96 is connected to ventilation system 12. For example, in some embodiments in which ventilation system 12 can provide either leakage ventilation or exhalation valve ventilation, gas delivery control system 31 may automatically select or switch to exhalation valve ventilation based on the determination that an exhalation valve 96 is connected to ventilation system 12.

In addition, gas delivery control system 31 may allow or disallow particular ventilation modes or settings based on the determination that an exhalation valve 96 is connected to ventilation system 12. For example, control system 31 may allow user or automatic selection of, and/or automatic switching to, certain ventilation modes or settings that require control of an exhalation valve 96.

At step 412, in example configurations in which ventilation system 12 selects or switches to exhalation valve ventilation (at step 410), gas delivery control system 31 may determine whether any selected ventilation settings are incompatible with exhalation valve ventilation. If so, gas delivery control system 31 may trigger an alarm at step 414 and wait for the user to adjust the selected settings to become compatible before beginning ventilation of patient 11. The alarm may comprise any notification that may be sensed by a user, e.g., an audible alarm or a visible alarm displayed to the user, e.g., via display 28 or separate device (e.g., an LED). If not, the method may continue to step 416.

At step 416, ventilation system 12 may provide breathing assistance to patient 11 according to a ventilation mode and/or settings (e.g., exhalation valve ventilation) determined at steps 410-414.

Returning to the decision at step 406, if exhalation valve detection system 34 determines that an exhalation valve 96 is not connected to ventilation system 12, the method may proceed to step 418.

At step 418, exhalation valve detection system 34 may generate and display a user notification or alarm that an exhalation valve 96 is not connected and may not be used for controlling breathing assistance. System 34 may provide the user an opportunity to connect an exhalation valve 96, or to select to continue without an exhalation valve 96, or alternatively the method may automatically continue to step 420.

At step 420, gas delivery control system 31 may automatically select between different ventilation modes or settings or otherwise control one or more ventilation parameters (e.g., flow and/or pressure) based on the determination that an exhalation valve 96 is not connected to ventilation system 12. For example, in some embodiments in which ventilation system 12 can provide either leakage ventilation or exhalation valve ventilation, gas delivery control system 31 may automatically select or switch to leakage ventilation based on the determination that an exhalation valve 96 is not connected to ventilation system 12.

In addition, gas delivery control system 31 may allow or disallow particular ventilation modes or settings based on the determination that an exhalation valve 96 is not connected to ventilation system 12. For example, control system 31 may disallow user or automatic selection of, and/or automatic switching to, certain ventilation modes or settings that require control of an exhalation valve 96.

At step 422, in example configurations in which ventilation system 12 selects or switches to leakage ventilation (at step 410), gas delivery control system 31 may determine whether any selected ventilation settings are incompatible with leakage ventilation. If so, gas delivery control system 31 may trigger an alarm at step 424 and wait for the user to adjust the selected settings to become compatible before beginning ventilation of patient 11. The alarm may comprise any notification that may be sensed by a user, e.g., an audible alarm or a visible alarm displayed to the user, e.g., via display 28 or separate device (e.g., an LED). If not, the method may continue to step 426.

At step 426, ventilation system 12 may provide breathing assistance to patient 11 according to a ventilation mode and/or settings (e.g., leakage ventilation) determined at steps 420-424.

While providing breathing assistance to patient 11, exhalation valve detection system 34 may continue to determine whether an exhalation valve 96 is connected to system 12 periodically, continuously, in response to a detected event or user request, or at any other time. In this manner, control system 22 may adjust to a connection or disconnection of an exhalation valve 96 while system 12 is providing breathing assistance to patient 11. Such detection may include, for example, the techniques discussed above at steps 402-406.

As shown at step 428, if exhalation valve detection system 34 detects a disconnection of exhalation valve 96 while ventilation system 12 is providing breathing assistance, the method may advance to steps 418-416 to account for the disconnection. This may include, e.g., generating a user alarm and automatically adjusting one or more ventilation settings (e.g., switching from exhalation valve ventilation to leakage ventilation).

Similarly, as shown at step 430, if exhalation valve detection system 34 detects a connection/re-connection of exhalation valve 96 while ventilation system 12 is providing breathing assistance, the method may advance to steps 408-416 to account for the connection/re-connection. This may include, e.g., generating a user notification and automatically adjusting one or more ventilation settings (e.g., switching from leakage ventilation to exhalation valve ventilation).

Figures 11, 12:
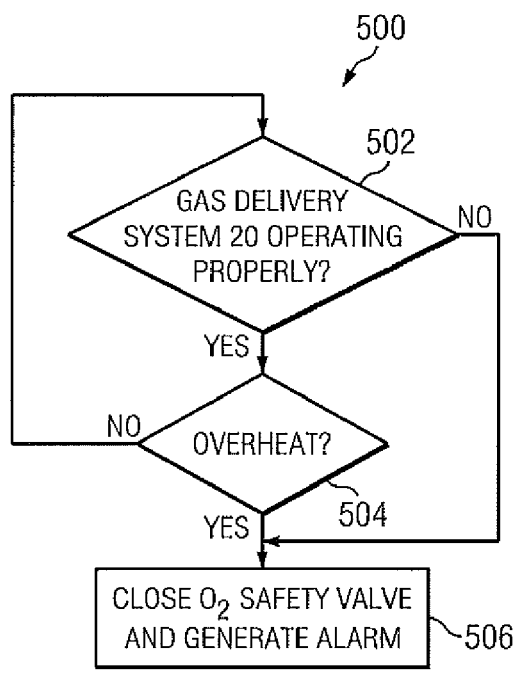
FIG. 11 illustrates an example method for managing a supplemental gas supply (e.g., supplemental oxygen supply) in a breathing assistance system, according to certain embodiments of the present disclosure.
FIG. 12 illustrates an example method for determining an overheat condition in a breathing assistance system and managing a supplemental gas flow (e.g., supplemental oxygen flow) using an $O_2$ safety system as shown in FIG. 4A, according to certain embodiments of the present disclosure.

FIG. 11 illustrates an example method 500 for managing a supplemental gas supply (e.g., supplemental oxygen supply) in a breathing assistance system 10 configured to provide breathing assistance to a patient 11, according to certain embodiments of the present disclosure. In particular, method 500 may provide security for a supplemental gas supply when a gas delivery system 20 of breathing assistance system 10 is overheating or not operating properly (e.g., not running). For example, $O_2$ safety system 38 may stop or slow the flow of the supplemental gas (e.g., by closing a safety valve) in such situations. Although the discussion focuses on a supplemental oxygen supply, the same techniques may be used for any other type of supplemental gas supply.

At step 502, $O_2$ safety system 38 may determine whether gas delivery system 20 is operating properly (e.g., not running or running improperly). For example, $O_2$ safety system 38 may communicate with gas delivery control system 31 to obtain data regarding the operation of gas delivery system 20. If $O_2$ safety system 38 determines that gas delivery system 20 is not operating properly, the method may proceed to step

506. Otherwise, if $O_2$ safety system 38 determines that gas delivery system 20 is operating properly, the method may proceed to step 504.

At step 504, $O_2$ safety system 38 (e.g., an overheat detection module 158 of system 38) may determine whether gas delivery system 20 is overheating by monitoring readings from a temperature sensor 83 configured to measure the temperature of gas delivery system 20 or a component thereof. For example, overheat detection module 158 may compare readings from temperature sensor 83 with threshold temperature(s) to determine whether gas delivery system 20 is overheating. If $O_2$ safety system 38 determines that gas delivery system 20 is overheating, the method may proceed to step 506. Otherwise, if $O_2$ safety system 38 determines that gas delivery system 20 is not overheating, the method may return to step 502.

Steps 502 and 504 may be performed in any order and/or substantially simultaneously. Steps 502 and 504 may be performed at any time, e.g., substantially continuously, periodically, or in response to a triggering event.

At step 506, in response to determining that gas delivery system 20 is not operating properly (at step 502) or that gas delivery system 20 is overheating (at step 504), overheat detection module 158 may send an overheat notification signal to gas delivery control system 31. Based on such signal, gas delivery control system 31 may control O2 safety valve and/or gas delivery system 20 accordingly. For example, gas delivery control system 31 may partially or fully close O2 safety valve to slow or stop the flow of supplemental oxygen.

FIG. 12 illustrates an example method 550 for determining an overheat condition in a breathing assistance system 10 and managing a supplemental gas flow (e.g., supplemental oxygen flow) accordingly, according to certain embodiments of the present disclosure. In general, method 550 is an example embodiment of steps 504 and 506 of method 500 shown in FIG. 11. More particularly, method 550 may monitor for an overheat condition in a gas delivery system 20, and in response to detecting an overheat condition, stop or slow the flow of the supplemental gas (e.g., by closing a safety valve). Again, although the discussion focuses on a supplemental oxygen supply, the same techniques may be used for any other type of supplemental gas supply.

At step 552, overheat detection module 158 may monitor temperature readings from temperature sensor 83 configured to measure the temperature of gas delivery system 20 or a component thereof. Temperature sensor 83 may take and communicate measurement signals to overheat detection module 158 at any time, e.g., substantially continuously, periodically, or in response to a triggering event.

At step 552, overheat detection module 158 may compare temperature readings from temperature sensor 83 with a threshold temperature to determine whether gas delivery system 20 is overheating. Such threshold temperature may be constant or may change over time. For example, a threshold temperature may be determined using an algorithm or look-up table relating the threshold value to one or more other parameters, e.g., the current pressure or flow rate of gas delivered by delivery system 20, or the current speed of a turbine (in embodiments in which gas delivery system 20 comprises a turbine-based blower). Thus, for example, an algorithm may be used to increase the threshold temperature in proportion to the flow rate or turbine speed, as higher temperatures are expected with higher flow rates or turbine speeds.

As another example, the threshold temperature may be selected based on the current ventilation mode or settings. For example, different threshold temperatures may be used for SIMV ventilation, Assist/Control ventilation, and CPAP ventilation. As another example, different threshold temperatures may be used for adult vs. pediatric ventilation, as higher temperatures are expected with adult ventilation (e.g., due to higher flow rates or turbine speeds).

At step 556, overheat detection module 158 may determine whether gas delivery system 20 is overheating based on any number of temperature readings and comparisons performed at steps 552 and 554. For example, overheat detection module 158 may determine an overheat condition in response to a single sensor reading above the relevant threshold temperature. As another example, overheat detection module 158 may determine an overheat condition based on a predetermined number (e.g., 5) of consecutive sensor readings above the relevant threshold temperature, based on sensor readings remaining above the relevant threshold temperature for a predetermined duration (e.g., 10 seconds). As another example, overheat detection module 158 may determine an overheat condition based on an average of sensor readings for a predetermined number of readings or over a predetermined duration.

If overheat detection module 158 detects an overheat condition at step 556, the method may proceed to step 558. At step 558, control system 22 may control (e.g., reduce or stop) the supplemental gas flow and generate an alarm, in response to detecting an overheat condition at step 556. For example, overheat detection module 158 may send an overheat notification signal to gas delivery control system 31, which may in turn control O2 safety valve 156 and/or gas delivery system 20 accordingly. For example, gas delivery control system 31 may partially or fully close O2 safety valve 156 to slow or stop the flow of supplemental oxygen.

Overheat detection module 158 and/or gas delivery control system 31 may generate any suitable alarm(s) 159 regarding the overheat condition and/or the closing of O2 safety valve 156. An alarm 159 may comprise any notification that may be sensed by a user, e.g., audible alarm or a visible alarm displayed to the user.

If overheat detection module 158 does not detect an overheat condition at step 556, the method may proceed to step 560. At step 560, overheat detection module 158 may determine to adjust the temperature threshold used at step 554. For example, the threshold temperature may be adjusted (e.g., using an algorithm or look-up table) at step 562 according to one or more current ventilation parameters (e.g., the current pressure or flow rate of gas delivered by delivery system 20, or the current speed of a turbine). Thus, for example, overheat detection module 158 automatically increase the temperature threshold (according to an algorithm or look-up table) in response to an increase in the current flow rate or turbine speed, as higher temperatures are expected with higher flow rates or turbine speeds.

As another example, overheat detection module 158 may automatically adjust the temperature threshold based on a change in the current ventilation mode or settings. For example, module 158 may adjust the temperature threshold in response to a switch from Assist/Control ventilation to CPAP ventilation.

Figure 13A:
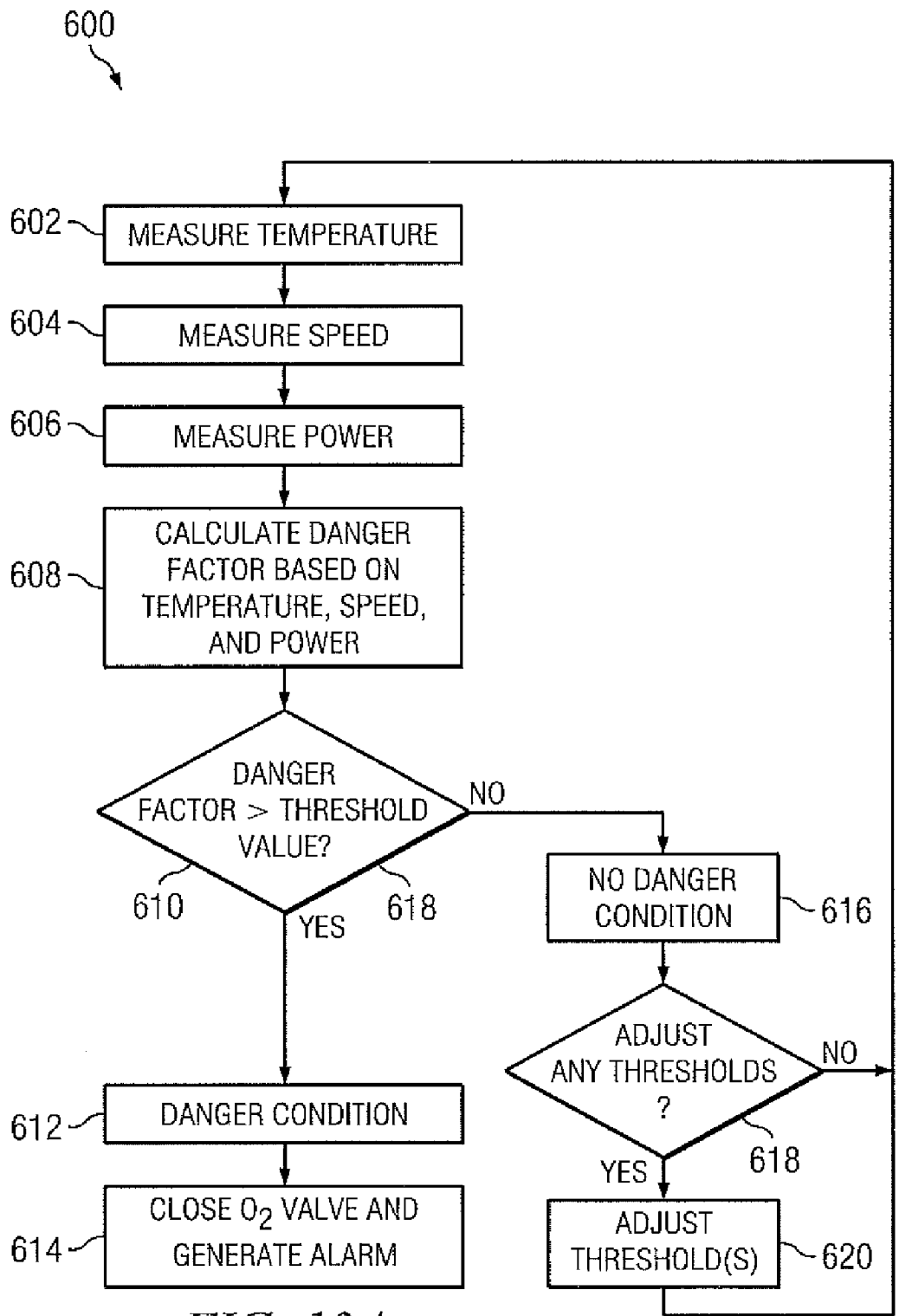
FIGS. 13A and 13B illustrate example methods for determining an overheat condition in a breathing assistance system and managing a supplemental gas flow (e.g., supplemental oxygen flow) using an $O_2$ safety system as shown in FIG. 4B, according to certain embodiments of the present disclosure.
Figure 13B:
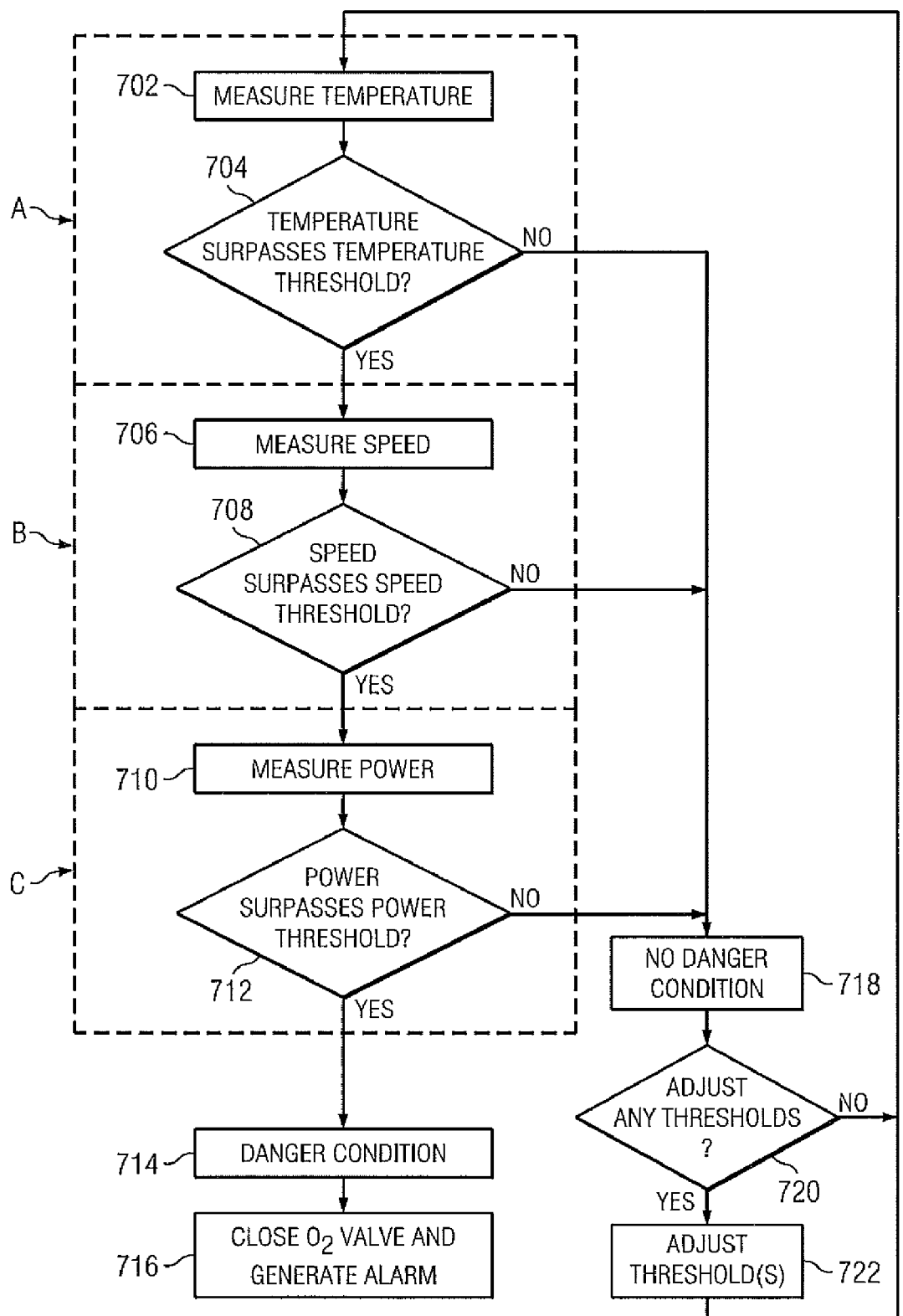

FIGS. 13A and 13B illustrate example methods 600 and 700 for determining a danger condition in a breathing assistance system and managing a supplemental gas flow (e.g., supplemental oxygen flow) using an $O_2$ safety system as shown in FIG. 4B, according to certain embodiments of the present disclosure.

Referring to FIG. 13A, method 600 may be performed at any time during the operation of ventilation system 12. At step 602, a temperature of gas delivery system 20 (e.g., a blower motor) may be measured, e.g., using temperature sensor 83. At step 604, an operational speed of a component (e.g., a motor, blower, turbine) of gas delivery system 20 may be measured, e.g., using a speed sensor 84. At step 606, the power drawn by a component (e.g., a motor, blower, turbine) of gas delivery system 20 may be measured, e.g., using a power monitor 85. Steps 602-606 may be performed in any order, and each step may be performed at any suitable time and frequency. In addition, in some embodiments, at least one of steps 602-606 may be excluded, e.g., in embodiments in which O₂ safety system is controlled using temperature and speed measurements, but not power measurements.

At step 608, a danger factor may be calculated based on the data obtained at steps 602-606. For example, safety status module 161 may calculate a safety factor using one or more algorithms relating the different types of measurements obtained at steps 602-606.

At step 610, safety status module 161 may compare the calculated safety factor to a danger condition threshold value to determine whether a danger condition is present. If it is determined that a danger condition is present (see step 612), control system 22 may slow or stop the supplemental oxygen flow (e.g., by controlling O2 safety valve 156) and generate an alarm at step 614.

Alternatively, if it is determined that a danger condition is not present (see step 616), the method may advance to step 618. At step 618, safety status module 161 may determine to adjust the danger factor threshold value used at step 610. For example, the threshold value may be adjusted (e.g., using an algorithm or look-up table) at step 620 according to the current ventilation mode or current ventilation parameters. The method may then return to steps 602-606 for continued measurements.

Referring to FIG. 13B, method 700 may be performed at any time during the operation of ventilation system 12. At step 702, a temperature of gas delivery system 20 (e.g., a blower motor) may be measured, e.g., using temperature sensor 83. At step 704, safety status module 161 may compare the measured temperature to a temperature threshold value. If the measured temperature does not surpass the temperature threshold value, there is no danger condition present, and the method may continue to step 718.

However, if the measured temperature does surpass the temperature threshold value, the method continues to step 706 for further analysis to determine whether a danger condition is present. At step 706, an operational speed of a component (e.g., a motor, blower, turbine) of gas delivery system 20 may be measured, e.g., using a speed sensor 84. At step 708, safety status module 161 may compare the measured speed to a speed threshold value. If the measured speed does not surpass the speed threshold value, there is no danger condition present, and the method may continue to step 718.

However, if the measured speed does surpass the speed threshold value, the method continues to step 710 for further analysis to determine whether a danger condition is present. At step 710, the power drawn by a component (e.g., a motor, blower, turbine) of gas delivery system 20 may be measured, e.g., using a power monitor 85. If the measured power does not surpass the power threshold value, there is no danger condition present, and the method may continue to step 718.

However, if the measured power does surpass the power threshold value (in combination with the temperature and speed surpassing their corresponding threshold values, as described above), a danger condition is identified at 714. In response to identifying the danger condition, control system 22 may slow or stop the supplemental oxygen flow (e.g., by controlling O2 safety valve 156) and generate an alarm at step 716.

As discussed above, if any of the measured temperature, speed, or power do not surpass their corresponding thresholds, there is no danger condition present, as indicated at step 718. At step 720, safety status module 161 may determine to adjust one or more threshold values used at steps 704, 708, and/or 712. For example, the speed threshold value may be adjusted (e.g., using an algorithm or look-up table) at step 722 according to the current ventilation mode or current ventilation parameters. The method may then return to step 702.

Certain steps may be eliminated from method 700 depending on which of temperature, speed, and power measurements are used for controlling O₂ safety system, according to the particular embodiment. Thus, any of the method modules "A", "B", or "C" shown in FIG. 13B may be removed from method 700, depending on the particular embodiment. For example, in embodiments in which temperature and speed measurements, but not power measurements, are used for controlling O₂ safety system, steps 710 and 712 indicated as method module "C" may be removed from method 700. As another example, in embodiments in which speed and power measurements, but not temperature measurements, are used for controlling O₂ safety system, steps 702 and 704 indicated as method module "A" may be removed from method 700.

It should be understood that various changes, substitutions and alterations can be made herein without departing from the spirit and scope of the disclosure as illustrated by the following claims.

What is claimed is:

1. A method for managing a supplemental gas supply in a breathing assistance system configured to provide breathing assistance to a patient, the method comprising:
    monitoring a temperature associated with a breathing assistance system configured to deliver a first gas and a supplemental gas toward a patient;
    comparing the monitored temperature to a threshold temperature;
    automatically and dynamically adjusting the threshold temperature based on at least one non-temperature parameter selected from the group consisting of: a detected pressure, a detected flow rate, and a detected motor or turbine speed; and
    automatically controlling the flow of the supplemental gas based at least on the comparison of the monitored temperature with the dynamically adjusted threshold temperature.

2. A method according to claim 1, wherein automatically controlling the flow of the supplemental gas comprises at least partially closing a valve associated with the supplemental gas flow.

3. A method according to claim 1, comprising: determining an overheat condition based at least on the monitored temperature associated with the breathing assistance system; and automatically reducing the flow of the supplemental gas based at least on the determination of an overheat condition.

4. A method according to claim 3, wherein determining an overheat condition comprises comparing the monitored temperature associated with the breathing assistance system with a threshold temperature.

5. A method according to claim 1, further comprising: monitoring an operational speed of a gas delivery system component of the breathing assistance system; and automatically controlling the flow of the supplemental gas based at least on (a) the monitored temperature and (b) the monitored operational speed of the gas delivery system component.

6. A method for managing a supplemental gas supply in a breathing assistance system configured to provide breathing assistance to a patient, the method comprising:
    monitoring temperature associated with a assistance system configured to deliver a first gas and a supplemental gas toward a patent; and
    monitoring a measure of power drawn by a gas delivery system component of the breathing assistance system; and
    automatically controlling the flow of the supplemental gas based at least on (a) the monitored temperature and (b) the monitored measure of power drawn by the gas delivery system component.

7. A method according to claim 6, further comprising:
    monitoring an operational speed of a gas delivery system component of the breathing assistance system; monitoring a measure of power drawn by the gas delivery system component; and automatically controlling the flow of the supplemental gas based at least on (a) the monitored temperature, (b) the monitored operational speed of the gas delivery system component, and (c) the monitored measure of power drawn by the gas delivery system component.

8. A method for managing a supplemental gas supply in a breathing assistance system configured to provide breathing assistance to a patient, comprising:
    monitoring temperature associated with a assistance system configured to deliver a first gas and a supplemental gas toward a patent; and
    determining a first overheat condition if the monitored temperature exceeds a first temperature threshold;
    determining a second overheat condition if the monitored temperature exceeds a second temperature threshold different from the first threshold;
    automatically reducing the flow of the supplemental gas based at least on a determination of a first overheat condition; and
    automatically controlling the flow of the first gas based at least on a determination of a second overheat condition.

9. A method according to claim 8, further comprising automatically adjusting the threshold temperature.

10. A method according to claim 8, wherein the second temperature threshold is greater than the first threshold.

11. A method according to claim 1, wherein the first gas comprises air and the supplemental gas comprises supplemental oxygen.

12. A system for managing a supplemental gas supply in a breathing assistance system configured to provide breathing assistance to a patient, the system comprising:
    a temperature sensor configured to measure a temperature associated with a breathing assistance system configured to deliver a first gas and a supplemental gas toward a patient;
    a control system configured to:
        comparing the measured temperature to a threshold temperature;
        automatically and dynamically adjusted the threshold temperature based on at least one non-temperature parameter selected from the group consisting of: a detected pressure, a detected flow rate, and a detected motor or turbine speed; and
        automatically control the flow of the supplemental gas based at least on the comparison of the measured temperature with the dynamically adjusted threshold temperature.

13. A system according to claim 12, further comprising: a valve associated with the supplemental gas flow; and wherein the control system is configured to at least partially close the valve associated with the supplemental gas flow based at least on the monitored temperature.

14. A system according to claim 12, comprising: an overheat detection module configured to determine an overheat condition based at least on the monitored temperature associated with the breathing assistance system; and the control system is configured to automatically reduce the flow of the supplemental gas based at least on the determination of an overheat condition.

15. A system according to claim 14, wherein determining an overheat condition comprises comparing the monitored temperature associated with the breathing assistance system with a threshold temperature.

16. A system for managing a supplement gas supply in a breathing assistance system configured to provide breathing assistance to a patient, the system comprising:
    a temperature sensor configured to measure a temperature associated with a breathing assistance system configured to deliver a first gas and a supplemental gas toward a patient;
    an overheat detection module configured to:
        determine a first overheat condition if the monitored temperature exceeds a first temperature threshold; and
        determine a second overheat condition if the monitored temperature exceeds a second temperature threshold different from the first threshold; and
    an control system configured to:
        automatically reduce the supplemental gas supply in response to determining a first overheat condition; and
        automatically control the gas delivery system in response to determining a second overheat condition.

17. A system according to claim 16, wherein the overheat detection module is configured to automatically adjust the threshold temperature and the second temperature threshold.

18. A system according to claim 16, wherein the second temperature threshold is greater than the first threshold.

19. A system according to claim 12, further comprising: a speed sensor configured to monitor an operational speed of a gas delivery system component of the breathing assistance system; and wherein the control system is configured to automatically control the flow of the supplemental gas based at least on (a) the monitored temperature and (b) the monitored operational speed of the gas delivery system component.

20. A managing a supplement gas supply in a breathing assistance system configured to provide breathing assistance to a patient, the system comprising:
    a temperature sensor configured to measure a temperature associated with a breathing assistance system configured to deliver a first gas and a supplemental gas toward a patient;
    a power monitor configured to monitor a measure of power drawn by a gas delivery system component of the breathing assistance system; and
    a control system configured to automatically control the flow of the supplemental gas based at least on (a) the monitored temperature and (b) the monitored measure of power drawn by the gas delivery system component.

21. A method according to claim 20, further comprising:
    a speed sensor configured to measure an operational speed of a gas delivery system component of the breathing assistance system; and
    wherein the control system is configured to automatically control the flow of the supplemental gas based at least on (a) the measured temperature, (b) the monitored operational speed of the gas delivery system component, and (c) the monitored measure of power drawn by the gas delivery system component.

* * * * *